US011851709B2

(12) United States Patent
Prat Aparicio et al.

(10) Patent No.: US 11,851,709 B2
(45) Date of Patent: Dec. 26, 2023

(54) HER2 AS A PREDICTOR OF RESPONSE TO DUAL HER2 BLOCKADE IN THE ABSENCE OF CYTOTOXIC THERAPY

(71) Applicants: FUNDACIÓ PRIVADA INSTITUT D'INVESTIGACIÓ ONCOLÓGICA DE VALL D'HEBRON, Barcelona (ES); FUNDACIÓN SOLTI, Barcelona (ES); FUNDACIÓN PARA EL FOMENTO DE LA INVESTIGACIÓN SANITARIA Y BIOMÉDICA DE LA COMUNITAT VALENCIANA, Valencia (ES); HOSPITAL CLÍNIC DE BARCELONA, Barcelona (ES)

(72) Inventors: Aleix Prat Aparicio, Barcelona (ES); Javier Cortés Castán, Barcelona (ES); Antonio Llombart Cussac, Valencia (ES)

(73) Assignees: FUNDACIÓ PRIVADA INSTITUT D'INVESTIGACIÓ ONCOLÓGICA DE VALL D'HEBRON, Barcelona (ES); FUNDACIÓN SOLTI, Barcelona (ES); FUNDACIÓN PARA EL FOMENTO DE LA INVESTIGACIÓN SANITARIA Y BIOMÉDICA DE LA COMUNITAT VALENCIANA, Barcelona (ES); HOSPITAL CLÍNIC DE BARCELONA, Barcelona (ES)

( * ) Notice: Subject to any disclaimer, the term of this patent is extended or adjusted under 35 U.S.C. 154(b) by 412 days.

(21) Appl. No.: 16/467,019

(22) PCT Filed: Dec. 7, 2016

(86) PCT No.: PCT/EP2016/080056
§ 371 (c)(1),
(2) Date: Jun. 5, 2019

(87) PCT Pub. No.: WO2018/103834
PCT Pub. Date: Jun. 14, 2018

(65) Prior Publication Data
US 2019/0338368 A1 Nov. 7, 2019

(51) Int. Cl.
*C12Q 1/68* (2018.01)
*C07H 21/04* (2006.01)
*C12Q 1/6886* (2018.01)

(52) U.S. Cl.
CPC ..... *C12Q 1/6886* (2013.01); *C12Q 2600/106* (2013.01); *C12Q 2600/158* (2013.01)

(58) Field of Classification Search
None
See application file for complete search history.

(56) References Cited

U.S. PATENT DOCUMENTS

| 2009/0203015 A1* | 8/2009 | Chang | C12Q 1/6886 |
| | | | 435/6.14 |
| 2010/0151463 A1 | 6/2010 | Baehner et al. | |
| 2011/0217297 A1* | 9/2011 | Kao | A61P 35/00 |
| | | | 514/249 |

FOREIGN PATENT DOCUMENTS

WO    WO 2011/031982 A1    3/2011

OTHER PUBLICATIONS

Yan et al. HER2 expression status in diverse cancers: review of results from 37,992 patients. Cancer Metastasis Rev; 2015; 34:157-164. (Year: 2015).*
Press et al. HER-2 Gene Amplification, HER-2 and Epidermal Growth Factor Receptor mRNA and Protein Expression, and Lapatinib Efficacy in Women with Metastatic Breast Cancer. Clin Cancer Res 2008;14(23): 7861-7870. (Year: 2008).*
Larsen et al. A systematic review of trastuzumab and lapatinib in the treatment of women with brain metastases from HER2-positive breast cancer. Cancer Treatment Reviews; 2013; 39: 720-727. (Year: 2013).*
Madarnas et al. Adjuvant/neoadjuvant trastuzumab therapy in women with HER-2/neu-overexpressing breast cancer: A systematic review. Cancer Treatment Reviews; 2008; 34: 539-557. (Year: 2008).*
Sawaki et al. Evaluation of Trastuzumab Without Chemotherapy as a Post-operative Adjuvant Therapy in HER2-positive Elderly Breast Cancer Patients: Randomized Controlled Trial [Respect (N-SAS BC07)]. Jpn J Clin Onco.; 2011; 41(5): 709-712. (Year: 2011).*

(Continued)

*Primary Examiner* — Jeanine A Goldberg
(74) *Attorney, Agent, or Firm* — SQUIRE PATTON BOGGS (US) LLP

(57) ABSTRACT

The present invention refers to an in vitro method for determining the efficacy of anti-HER2 therapy in the absence of chemotherapy in a patient with HER2+ breast cancer comprising the detection and/or quantification of the expression of HER2 in an isolated biological sample of the patient, either (1) before or (2) before and during the anti-HER2 therapy in the absence of chemotherapy treatment. The present invention also refers to the use of a gene expression product of HER2 as a as an in vitro marker for determining the efficacy of anti-HER2 therapy in the absence of chemotherapy in a patient with HER2+ breast cancer, or alternatively as an in vitro marker for deciding or recommending whether to initiate an alternative medical regime to anti-HER2 therapy without chemotherapy in a patient with HER2+ breast cancer.

6 Claims, 9 Drawing Sheets
Specification includes a Sequence Listing.

(56) References Cited

OTHER PUBLICATIONS

Baselga. Clinical trials of Herceptin1 (trastuzumab). European Journal of Cancer; 2001; 37: S18-S24. (Year: 2001).*
Heyde et al. mRNA Profiling Reveals Determinants of Trastuzumab Efficiency in HER2-Positive Breast Cancer. PLOS One; 2015; 10(2): e0117818: 1-27. (Year: 2015).*
Tanioka et al. Transcriptional CCND1 expression as a predictor of poor response to neoadjuvant chemotherapy with trastuzumab in HER2-positive/ER-positive breast cancer. Breast Cancer Res Treat ; 2014; 147:513-525. (Year: 2014).*
Rimawi et al. Multicenter Phase II Study of Neoadjuvant Lapatinib and Trastuzumab With Hormonal Therapy and Without Chemotherapy in Patients With Human Epidermal Growth Factor Receptor 2-Overexpressing Breast Cancer: TBCRC 006. J Clin Oncol.; 2013; 31:1726-1731. (Year: 2013).*
Baselga et al. Lapatinib with trastuzumab for HER2-positive early breast cancer (NeoALTTO): a randomised, open-label, multicentre,phase 3 trial. Lancet ; 2012; 379: 633-640. (Year: 2012).*
Noske et al. Comparison of different approaches for assessment of HER2 expression on protein and mRNA level: prediction of chemotherapy response in the neoadjuvant GeparTrio trial (NCT00544765). Breast Cancer Res Treat; 2011; 126:109-117. (Year: 2011).*
Mittendorf et al. Loss of HER2 Amplification Following Trastuzumab-based Neoadjuvant Systemic Therapy and Survival Outcomes. Clin Cancer Res.; 2009; 15(23): 7381-7388. (Year: 2009).*
Yan et al. Cancer Metastasis Rev; 2015; 34:157-164. (Year: 2015).*
Press et al. Clin Cancer Res 2008;14(23): 7861-7870. (Year: 2008).*
Larsen et al. Cancer Treatment Reviews; 2013; 39: 720-727 (Review). (Year: 2013).*
Madarnas et al. Cancer Treatment Reviews; 2008; 34: 539-557 (Review). (Year: 2008).*
Sawaki et al. Jpn J Clin Onco.; 2011; 41(5): 709-712. (Year: 2011).*
Noske et al. Breast Cancer Res Treat; 2011; 126:109-117. (Year: 2011).*
Mittendorf et al. Clin Cancer Res.; 2009; 15(23): 7381-7388. (Year: 2009).*
Baselga. European Journal of Cancer; 2001; 37: S18-S24. (Year: 2001).*
Heyde et al. PLOS One; 2015; 10(2): e0117818: 1-27. (Year: 2015).*
Tanioka et al. Breast Cancer Res Treat; 2014; 147:513-525. (Year: 2014).*
Rimawi et al. Cancer: TBCRC 006. J Clin Oncol.; 2013; 31:1726-1731. (Year: 2013).*
Mohsin et al. (J. of Clinical Oncology, vol. 23, No. 11, pp. 2460-2468, 2005) (Year: 2005).*
Kramer-Marek et al. (Proceedings of the 2010 World Molecular Imaging Congress, S564, Presentation No. 0074) (Year: 2010).*
Shimizu et al. (Breast Cancer, vol. 23, pp. 624-632, 2016) (Year: 2016).*
Esteva et al. (Nat. Rev. Clin. Oncology, vol. 7, pp. 98-107, 2010) (Year: 2010).*
Mittendorf, et al, "Cancer Therapy: Clinical—Loss of HER2 amplification following Trastuzumab-based neoadjuvant systemic therapy and survival outcomes", Clinical Cancer Research; Dec. 1, 2009 (published online Nov. 17, 2009); vol. 15(23), pp. 7381-7388, doi:10.1158/1078-0432.CCR-09-1735.
International Search Report and Written Opinion dated Aug. 30, 2017 for PCT Application No. PCT/EP2016/080056, 17 pages.
Advani, et al, "Dual HER2 blockade in the neoadjuvant and adjuvant treatment of HER2-positive breast cancer", Breast Cancer: Targets and Therapy, Sep. 1, 2015, vol. 7, pp. 321-325, doi:10.2147/BCTT.S90627.
Baselga, et al, "Lapatinib with trastuzumab for HER2-positive early breast cancer (NeoALTTO): a randomised, open-label, multicentre, phase 3 trial", The Lancet, Feb. 18, 2012, vol. 379, pp. 633-640.
Baselga, et al, "Pertuzumab plus Trastuzumab plus Docetaxel for Metastatic Breast Cancer", The New England Journal of Medicine, Jan. 12, 2012, vol. 366, No. 2, pp. 109-119.
Blackwell, et al, "Overall Survival Benefit With Lapatinib in Combination With Trastuzumab for Patients With Human Epidermal Growth Factor Receptor 2-Positive Metastatic Breast Cancer: Final Results From the EGF104900 Study", Journal of Clinical Oncology, Jul. 20, 2012; vol. 30, No. 21, pp. 2585-2592.
Carey, et al, "Molecular Heterogeneity and Response to Neoadjuvant Human Epidermal Growth Factor Receptor 2 Targeting in CALGB 40601, a Randomized Phase III Trial of Paclitaxel Plus Trastuzumab With or Without Lapatinib", Journal of Clinical Oncology 2015, published online Nov. 2, 2015, vol. 34, No. 6, pp. 542-549, with Appenix, 15 pages.
Cortazar, et al, "Pathological complete response and long-term clinical benefit in breast cancer: the CTNeoBC pooled analysis", The Lancet, Jul. 12, 2014, vol. 384, pp. 164-172.
Cortes, et al, "Pertuzumab Monotherapy After Trastuzumab-Based Treatment and Subsequent Reintroduction of Trastuzumab: Activity and Tolerability in Patients With Advanced Human Epidermal Growth Factor Receptor 2-Positive Breast Cancer", Journal of Clinical Oncology, May 10, 2012, vol. 30, No. 14, pp. 1594-1600.
Fumagalli, et al, "RNA sequencing to predict response to neoadjuvant Anti-HER2 Therapy: A secondary analysis of the NeoALTTO randomized clinical trial", JAMA Oncology|Original Investigation, Sep. 29, 2016, pp. E1-E8.
Gianni, et al, "Efficacy and safety of neoadjuvant pertuzumab and trastuzumab in women with locally advanced, inflammatory, or early HER2-positive breast cancer (NeoSphere): a randomised multicentre, open-label, phase 2 trial", The Lancet Oncology, Jan. 2012, vol. 13, No. 1, pp. 25-32.
Hayes, et al, "HER2 and Response to Paclitaxel in Node-Positive Breast Cancer", The New England Journal of Medicine, Oct. 11, 2007, vol. 357, No. 15, pp. 1496-1506.
Montemurro, et al., "Potential biomarkers of long-term benefit from single-agent trastuzumab or lapatinib in HER2-positive metastatic breast cancer", Molecular Oncology 2014, Sep. 13, 2013, Elsevier, Amsterdam, NL, vol. 8, No. 1., pp. 20-26, doi:10.1016.
Piccart-Gebhart, et al, "Adjuvant Lapatinib and Trastuzumab for Early Human Epidermal Growth Factor Receptor 2-Positive Breast Cancer: Results From the Randomized Phase III Adjuvant Lapatinib and/or Trastuzumab Treatment Optimization Trial", Journal of Clinical Oncology, Apr. 1, 2016, vol. 34, No. 10, pp. 1034-1042, with Appenix, 25 pages.
Rimawi, et al, "Multicenter Phase II Study of Neoadjuvant Lapatinib and Trastuzumab With Hormonal Therapy and Without Chemotherapy in Patients With Human Epidermal Growth Factor Receptor 2-Overexpressing Breast Cancer: TBCRC 006", Journal of Clinical Oncology, May 10, 2013, vol. 31, No. 14, pp. 1726-1731.
Schneeweiss, et al, "Pertuzumab plus trastuzumab in combination with standard neoadjuvant anthracycline-containing and anthracycline-free chemotherapy regimens in patients with HER2-positive early breast cancer: a randomized phase II cardiac safety study (Tryphaena)", Annals of Oncology, May 22, 2013, vol. 24, No. 9, pp. 2278-2284.
Scaltriti, et al, "High HER2 Expression Correlates with Response to the Combination of Lapatinib and Trastuzumab", Clinical Cancer Research 2015, published online Dec. 2, 2014, vol. 21, No. 3, pp. 569-576.
Slamon, et al, "Adjuvant Trastuzumab in HER2-Positive Breast Cancer", The New England Journal of Medicine, Oct. 6, 2011, vol. 365, No. 14, pp. 1273-1283.
Tolaney, et al, "Adjuvant Paclitaxel and Trastuzumab for Node-Negative, HER2-Positive Breast Cancer", The New England Journal of Medicine, Jan. 8, 2015, vol. 372, No. 2, pp. 134-141.
Wolff, et al, "Recommendations for Human Epidermal Growth Factor Receptor 2 Testing in Breast Cancer: American Society of Clinical Oncology/College of American Pathologists Clinical Practice Guideline Update", Journal of Clinical Oncology, Nov. 1, 2013, vol. 31, No. 31, pp. 3997-4013, with Appendix, 18 pages.

* cited by examiner

SEQUENCE LISTING

<160> NUMBER OF SEQ ID NOS: 3

<210> SEQ ID NO 1
<211> LENGTH: 4816
<212> TYPE: DNA
<213> ORGANISM: Homo sapiens

<400> SEQUENCE: 1

```
gttcccggat ttttgtgggc gcctgccccg ccccctcgtcc ccctgctgtg tccatatatc     60
gaggcgatag ggttaaggga aggcggacgc ctgatgggtt aatgagcaaa ctgaagtgtt    120
ttccatgatc ttttttgagt cgcaattgaa gtaccacctc ccgagggtga ttgcttcccc    180
atgcggggta gaacctttgc tgtcctgttc accactctac ctccagcaca gaatttggct    240
tatgcctact caatgtgaag atgatgagga tgaaaacctt tgtgatgatc cacttccact    300
taatgaatgg tggcaaagca aagctatatt caagaccaca tgcaaagcta ctccctgagc    360
aaagagtcac agataaaacg ggggcaccag tagaatggcc aggacaaacg cagtgcagca    420
cagagactca gaccctggca gccatgcctg cgcaggcagt gatgagagtg acatgtactg    480
ttgtggacat gcacaaaagt gagtgtgcac cggcacagat atgaagctgc ggctccctgc    540
cagtcccgag acccacctgg acatgctccg ccacctctac cagggctgcc aggtggtgca    600
gggaaacctg gaactcacct acctgcccac caatgccagc ctgtccttcc tgcaggatat    660
ccaggaggtg cagggctacg tgctcatcgc tcacaaccaa gtgaggcagg tcccactgca    720
gaggctgcgg attgtgcgag gcacccagct ctttgaggac aactatgccc tggccgtgct    780
agacaatgga gacccgctga caataccac ccctgtcaca ggggcctccc caggaggcct    840
gcgggagctg cagcttcgaa gcctcacaga gatcttgaaa ggagggggtct tgatccagcg    900 gaaccccag ctctgctacc aggacacgat tttgtggaag gacatcttcc acaagaacaa    960
ccagctggct ctcacactga tagacaccaa ccgctctcgg gcctgccacc cctgttctcc    1020
gatgtgtaag ggctcccgct gctggggaga gagttctgag gattgtcaga gcctgacgcg    1080
cactgtctgt gccggtggct gtgcccgctg caagggggcca ctgcccactg actgctgcca    1140
tgagcagtgt gctgccggct gcacgggccc caagcactct gactgcctgg cctgcctcca    1200
cttcaaccac agtggcatct gtgagctgca ctgcccagcc ctggtcacct acaacacaga    1260
cacgtttgag tccatgccca atcccgaggg ccggtataca ttcggcgcca gctgtgtgac    1320
tgcctgtccc tacaactacc tttctacgga cgtgggatcc tgcaccctcg tctgcccccct    1380 gcacaaccaa gaggtgacag cagaggatgg aacacagcgg tgtgagaagt gcagcaagcc    1440
ctgtgcccga gtgtgctatg gtctgggcat ggagcacttg cgagaggtga gggcagttac    1500
cagtgccaat atccaggagt ttgctggctg caagaagatc tttgggagcc tggcatttct    1560
```

```
gccggagagc tttgatgggg acccagcctc aacactgcc ccgctccagc cagagcagct    1620
ccaagtgttt gagactctgg aagagatcac aggttaccta tacatctcag catggccgga    1680
cagcctgcct gacctcagcg tcttccagaa cctgcaagta atccgggac gaattctgca     1740
caatggcgcc tactcgctga ccctgcaagg gctgggcatc agctggctgg ggctgcgctc    1800
actgagggaa ctgggcagtg gactggccct catccaccat aacacccacc tctgcttcgt    1860
gcacacggtg ccctgggacc agctctttcg gaacccgcac caagtctgc tccacactgc     1920
caaccggcca gaggacgagt gtgtgggcga gggcctggcc tgccaccagc tgtgcgcccg    1980
agggcactgc tggggtccag ggcccaccca gtgtgtcaac tgcagccagt tccttcgggg    2040
ccaggagtgc gtggaggaat gccgagtact gcagggctc cccagggagt atgtgaatgc     2100
caggcactgt ttgccgtgcc accctgagtg tcagccccag aatggctcag tgacctgttt    2160
tggaccggag gctgaccagt gtgtggcctg tgcccactat aaggaccctc ccttctgcgt    2220
ggcccgctgc cccagcggtg tgaaacctga cctctcctac atgcccatct ggaagtttcc    2280
agatgaggag ggcgcatgcc agccttgccc catcaactgc acccactcct gtgtggacct    2340
ggatgacaag ggctgccccg ccgagcagag agccagccct ctgacgtcca tcatctctgc    2400
ggtggttggc attctgctgg tcgtggtctt ggggtggtc tttgggatcc tcatcaagcg     2460
acggcagcag aagatccgga agtacacgat gcggagactg ctgcaggaaa cggagctggt    2520
ggagccgctg acacctagcg gagcgatgcc caaccaggcg cagatgcgga tcctgaaaga    2580
gacggagctg aggaaggtga aggtgcttgg atctggcgct tttggcacag tctacaaggg    2640
catctggatc cctgatgggg agaatgtgaa aattccagtg gccatcaaag tgttgaggga    2700
aaacacatcc cccaaagcca acaaagaaat cttagacgaa gcatacgtga tggctggtgt    2760
gggctcccca tatgtctccc gccttctggg catctgcctg acatccacgg tgcagctggt    2820
gacacagctt atgcccatg gctgcctctt agaccatgtc cgggaaaacc gcggacgcct    2880
gggctcccag gacctgctga actggtgtat gcagattgcc aagggatga gctacctgga     2940
ggatgtgcgg ctcgtacaca gggacttggc cgctcggaac gtgctggtca agagtcccaa    3000
ccatgtcaaa attacagact cgggctggc tcggctgctg acattgacg agacagagta      3060
ccatgcagat gggggcaagg tgcccatcaa gtggatggcg ctggagtcca ttctccgccg    3120
gcggttcacc caccagagtg atgtgtgag ttatggtgtg actgtgtggg agctgatgac     3180
tttggggcc aaaccttacg atgggatccc agcccgggag atccctgacc tgctggaaaa    3240
gggggagcgg ctgccccagc cccccatctg caccattgat gtctacatga tcatggtcaa    3300
atgttggatg attgactctg aatgtcggcc aagattccgg gagttggtgt ctgaattctc    3360
ccgcatggcc agggaccccc agcgctttgt ggtcatccag aatgaggact gggcccagc    3420
cagtcccttg gacagcacct tctaccgctc actgctggag gacgatgaca tgggggacct    3480
ggtggatgct gaggagtatc tggtacccca gcagggcttc ttctgtccag acctgcccc    3540
gggcgctggg ggcatggtcc accacaggca ccgcagctca tctaccagga gtggcggtgg    3600
ggacctgaca ctagggctgg agccctctga agaggaggcc cccaggtctc cactggcacc    3660
ctccgaaggg gctggctccg atgtatttga tggtgacctg ggaatggggg cagccaaggg    3720
gctgcaaagc ctccccacac atgaccccag ccctctacag cggtacagtg aggacccac     3780
agtaccctg ccctctgaga ctgatggcta cgttgccccc ctgacctgca gcccccagcc    3840
tgaatatgtg aaccagccag atgttcggcc ccagccccct tcgccccgag agggccctct    3900
gcctgctgcc cgacctgctg gtgccactct ggaaaggccc aagactctct cccagggaa    3960
```

```
gaatgggggtc gtcaaagacg ttttttgcctt tgggggtgcc gtggagaacc ccgagtactt    4020
gacaccccag ggaggagctg ccccctcagcc ccaccctcct cctgccttca gcccagcctt    4080
cgacaacctc tattactggg accaggaccc accagagcgg ggggctccac ccagcacctt    4140
caaagggaca cctacggcag agaacccaga gtacctgggt ctggacgtgc agtgtgaac     4200 cagaaggcca agtccgcaga agccctgatg tgtcctcagg gagcagggaa ggcctgactt    4260
ctgctggcat caagaggtgg gagggccctc cgaccacttc caggggaacc tgccatgcca    4320
ggaacctgtc ctaaggaacc ttccttcctg cttgagttcc cagatggctg aaggggtcc    4380 agcctcgttg gaagaggaac agcactgggg agtctttgtg gattctgagg ccctgcccaa    4440
tgagactcta gggtccagtg gatgccacag cccagcttgg ccctttcctt ccagatcctg    4500
ggtactgaaa gccttaggga agctggcctg agagggggaag cggcccctaag ggagtgtcta   4560 agaacaaaag cgacccattc agagactgtc cctgaaacct agtactgccc cccatgagga    4620
aggaacagca atggtgtcag tatccaggct ttgtacagag tgcttttctg tttagttttt    4680 acttttttttg ttttgttttt ttaaagatga aataaagacc caggggggaga atgggtgttg   4740 tatggggagg caagtgtggg gggtccttct ccacacccac tttgtccatt tgcaaatata    4800
ttttggaaaa cagcta                                                     4816
```

<210> SEQ ID NO 2
<211> LENGTH: 1225
<212> TYPE: PRT
<213> ORGANISM: Homo sapiens

<400> SEQUENCE: 2

```
Met Lys Leu Arg Leu Pro Ala Ser Pro Glu Thr His Leu Asp Met Leu
1               5                   10                  15

Arg His Leu Tyr Gln Gly Cys Gln Val Val Gln Gly Asn Leu Glu Leu
            20                  25                  30

Thr Tyr Leu Pro Thr Asn Ala Ser Leu Ser Phe Leu Gln Asp Ile Gln
        35                  40                  45

Glu Val Gln Gly Tyr Val Leu Ile Ala His Asn Gln Val Arg Gln Val
    50                  55                  60

Pro Leu Gln Arg Leu Arg Ile Val Arg Gly Thr Gln Leu Phe Glu Asp
65                  70                  75                  80

Asn Tyr Ala Leu Ala Val Leu Asp Asn Gly Asp Pro Leu Asn Asn Thr
                85                  90                  95

Thr Pro Val Thr Gly Ala Ser Pro Gly Gly Leu Arg Glu Leu Gln Leu
            100                 105                 110

Arg Ser Leu Thr Glu Ile Leu Lys Gly Gly Val Leu Ile Gln Arg Asn
        115                 120                 125

Pro Gln Leu Cys Tyr Gln Asp Thr Ile Leu Trp Lys Asp Ile Phe His
    130                 135                 140

Lys Asn Asn Gln Leu Ala Leu Thr Leu Ile Asp Thr Asn Arg Ser Arg
145                 150                 155                 160

Ala Cys His Pro Cys Ser Pro Met Cys Lys Gly Ser Arg Cys Trp Gly
                165                 170                 175

Glu Ser Ser Glu Asp Cys Gln Ser Leu Thr Arg Thr Val Cys Ala Gly
            180                 185                 190

Gly Cys Ala Arg Cys Lys Gly Pro Leu Pro Thr Asp Cys Cys His Glu
        195                 200                 205

Gln Cys Ala Ala Gly Cys Thr Gly Pro Lys His Ser Asp Cys Leu Ala
```

-continued

```
            210                 215                 220
Cys Leu His Phe Asn His Ser Gly Ile Cys Glu Leu His Cys Pro Ala
225                 230                 235                 240

Leu Val Thr Tyr Asn Thr Asp Thr Phe Glu Ser Met Pro Asn Pro Glu
                    245                 250                 255

Gly Arg Tyr Thr Phe Gly Ala Ser Cys Val Thr Ala Cys Pro Tyr Asn
                260                 265                 270

Tyr Leu Ser Thr Asp Val Gly Ser Cys Thr Leu Val Cys Pro Leu His
            275                 280                 285

Asn Gln Glu Val Thr Ala Glu Asp Gly Thr Gln Arg Cys Glu Lys Cys
        290                 295                 300

Ser Lys Pro Cys Ala Arg Val Cys Tyr Gly Leu Gly Met Glu His Leu
305                 310                 315                 320

Arg Glu Val Arg Ala Val Thr Ser Ala Asn Ile Gln Glu Phe Ala Gly
                325                 330                 335

Cys Lys Lys Ile Phe Gly Ser Leu Ala Phe Leu Pro Glu Ser Phe Asp
                340                 345                 350

Gly Asp Pro Ala Ser Asn Thr Ala Pro Leu Gln Pro Glu Gln Leu Gln
            355                 360                 365

Val Phe Glu Thr Leu Glu Glu Ile Thr Gly Tyr Leu Tyr Ile Ser Ala
        370                 375                 380

Trp Pro Asp Ser Leu Pro Asp Leu Ser Val Phe Gln Asn Leu Gln Val
385                 390                 395                 400

Ile Arg Gly Arg Ile Leu His Asn Gly Ala Tyr Ser Leu Thr Leu Gln
                405                 410                 415

Gly Leu Gly Ile Ser Trp Leu Gly Leu Arg Ser Leu Arg Glu Leu Gly
                420                 425                 430

Ser Gly Leu Ala Leu Ile His His Asn Thr His Leu Cys Phe Val His
            435                 440                 445

Thr Val Pro Trp Asp Gln Leu Phe Arg Asn Pro His Gln Ala Leu Leu
        450                 455                 460

His Thr Ala Asn Arg Pro Glu Asp Glu Cys Val Gly Glu Gly Leu Ala
465                 470                 475                 480

Cys His Gln Leu Cys Ala Arg Gly His Cys Trp Gly Pro Gly Pro Thr
                485                 490                 495

Gln Cys Val Asn Cys Ser Gln Phe Leu Arg Gly Gln Glu Cys Val Glu
                500                 505                 510

Glu Cys Arg Val Leu Gln Gly Leu Pro Arg Glu Tyr Val Asn Ala Arg
            515                 520                 525

His Cys Leu Pro Cys His Pro Glu Cys Gln Pro Gln Asn Gly Ser Val
        530                 535                 540

Thr Cys Phe Gly Pro Glu Ala Asp Gln Cys Val Ala Cys Ala His Tyr
545                 550                 555                 560

Lys Asp Pro Pro Phe Cys Val Ala Arg Cys Pro Ser Gly Val Lys Pro
                565                 570                 575

Asp Leu Ser Tyr Met Pro Ile Trp Lys Phe Pro Asp Glu Glu Gly Ala
            580                 585                 590

Cys Gln Pro Cys Pro Ile Asn Cys Thr His Ser Cys Val Asp Leu Asp
        595                 600                 605

Asp Lys Gly Cys Pro Ala Glu Gln Arg Ala Ser Pro Leu Thr Ser Ile
        610                 615                 620

Ile Ser Ala Val Val Gly Ile Leu Leu Val Val Val Leu Gly Val Val
625                 630                 635                 640
```

```
Phe Gly Ile Leu Ile Lys Arg Arg Gln Gln Lys Ile Arg Lys Tyr Thr
                645                 650                 655

Met Arg Arg Leu Leu Gln Glu Thr Glu Leu Val Glu Pro Leu Thr Pro
            660                 665                 670

Ser Gly Ala Met Pro Asn Gln Ala Gln Met Arg Ile Leu Lys Glu Thr
        675                 680                 685

Glu Leu Arg Lys Val Lys Val Leu Gly Ser Gly Ala Phe Gly Thr Val
    690                 695                 700

Tyr Lys Gly Ile Trp Ile Pro Asp Gly Glu Asn Val Lys Ile Pro Val
705                 710                 715                 720

Ala Ile Lys Val Leu Arg Glu Asn Thr Ser Pro Lys Ala Asn Lys Glu
                725                 730                 735

Ile Leu Asp Glu Ala Tyr Val Met Ala Gly Val Gly Ser Pro Tyr Val
            740                 745                 750

Ser Arg Leu Leu Gly Ile Cys Leu Thr Ser Thr Val Gln Leu Val Thr
        755                 760                 765

Gln Leu Met Pro Tyr Gly Cys Leu Leu Asp His Val Arg Glu Asn Arg
    770                 775                 780

Gly Arg Leu Gly Ser Gln Asp Leu Leu Asn Trp Cys Met Gln Ile Ala
785                 790                 795                 800

Lys Gly Met Ser Tyr Leu Glu Asp Val Arg Leu Val His Arg Asp Leu
                805                 810                 815

Ala Ala Arg Asn Val Leu Val Lys Ser Pro Asn His Val Lys Ile Thr
            820                 825                 830

Asp Phe Gly Leu Ala Arg Leu Leu Asp Ile Asp Glu Thr Glu Tyr His
        835                 840                 845

Ala Asp Gly Gly Lys Val Pro Ile Lys Trp Met Ala Leu Glu Ser Ile
    850                 855                 860

Leu Arg Arg Arg Phe Thr His Gln Ser Asp Val Trp Ser Tyr Gly Val
865                 870                 875                 880

Thr Val Trp Glu Leu Met Thr Phe Gly Ala Lys Pro Tyr Asp Gly Ile
                885                 890                 895

Pro Ala Arg Glu Ile Pro Asp Leu Leu Glu Lys Gly Glu Arg Leu Pro
            900                 905                 910

Gln Pro Pro Ile Cys Thr Ile Asp Val Tyr Met Ile Met Val Lys Cys
        915                 920                 925

Trp Met Ile Asp Ser Glu Cys Arg Pro Arg Phe Arg Glu Leu Val Ser
    930                 935                 940

Glu Phe Ser Arg Met Ala Arg Asp Pro Gln Arg Phe Val Val Ile Gln
945                 950                 955                 960

Asn Glu Asp Leu Gly Pro Ala Ser Pro Leu Asp Ser Thr Phe Tyr Arg
                965                 970                 975

Ser Leu Leu Glu Asp Asp Asp Met Gly Asp Leu Val Asp Ala Glu Glu
            980                 985                 990

Tyr Leu Val Pro Gln Gln Gly Phe Phe Cys Pro Asp Pro Ala Pro Gly
        995                 1000                1005

Ala Gly Gly Met Val His His Arg His Arg Ser Ser Ser Thr Arg
    1010                1015                1020

Ser Gly Gly Gly Asp Leu Thr Leu Gly Leu Glu Pro Ser Glu Glu
    1025                1030                1035

Glu Ala Pro Arg Ser Pro Leu Ala Pro Ser Glu Gly Ala Gly Ser
    1040                1045                1050
```

```
Asp Val Phe Asp Gly Asp Leu Gly Met Gly Ala Ala Lys Gly Leu
    1055            1060                1065

Gln Ser Leu Pro Thr His Asp Pro Ser Pro Leu Gln Arg Tyr Ser
    1070            1075                1080

Glu Asp Pro Thr Val Pro Leu Pro Ser Glu Thr Asp Gly Tyr Val
    1085            1090                1095

Ala Pro Leu Thr Cys Ser Pro Gln Pro Glu Tyr Val Asn Gln Pro
    1100            1105                1110

Asp Val Arg Pro Gln Pro Pro Ser Pro Arg Glu Gly Pro Leu Pro
    1115            1120                1125

Ala Ala Arg Pro Ala Gly Ala Thr Leu Glu Arg Pro Lys Thr Leu
    1130            1135                1140

Ser Pro Gly Lys Asn Gly Val Val Lys Asp Val Phe Ala Phe Gly
    1145            1150                1155

Gly Ala Val Glu Asn Pro Glu Tyr Leu Thr Pro Gln Gly Gly Ala
    1160            1165                1170

Ala Pro Gln Pro His Pro Pro Pro Ala Phe Ser Pro Ala Phe Asp
    1175            1180                1185

Asn Leu Tyr Tyr Trp Asp Gln Asp Pro Pro Glu Arg Gly Ala Pro
    1190            1195                1200

Pro Ser Thr Phe Lys Gly Thr Pro Thr Ala Glu Asn Pro Glu Tyr
    1205            1210                1215

Leu Gly Leu Asp Val Pro Val
    1220            1225

<210> SEQ ID NO 3
<211> LENGTH: 100
<212> TYPE: DNA
<213> ORGANISM: Artificial Sequence
<220> FEATURE:
<223> OTHER INFORMATION: Target sequence of ERBB2

<400> SEQUENCE: 3
acagacacgt tgagtccat gcccaatccc gagggccggt atacattcgg cgccagctgt      60
gtgactgcct gtccctacaa ctacctttct acggacgtgg                          100
```

HER2 AS A PREDICTOR OF RESPONSE TO DUAL HER2 BLOCKADE IN THE ABSENCE OF CYTOTOXIC THERAPY

CROSS-REFERENCE TO RELATED APPLICATIONS

This application is a National Stage of International Patent Application No. PCT/EP2016/080056, filed Dec. 7, 2016 and published as WO 2018/103834 A1 on Jun. 14, 2018, entitled "HER2 AS A PREDICTOR OF RESPONSE TO DUAL HER2 BLOCKADE IN THE ABSENCE OF CYTOTOXIC THERAPY," the disclosure of which is incorporated herein by reference in its entirety. All patents and patent applications cited in this application, all related applications referenced herein, and all references cited therein are incorporated herein by reference in their entirety as if restated here in full and as if each individual patent and patent application was specifically and individually indicated to be incorporated by reference.

TECHNICAL FIELD

The present invention relates to the field of Medicine, particularly to breast cancer, especially to a new method for predicting the response to therapy against HER2 in HER2+ breast cancer patients that are not receiving chemotherapy. The method has potential applications in the clinical management and monitoring of said HER2+ breast cancer patients.

BACKGROUND ART

The HER2+ breast cancer, defined by IHC/FISH (standard definition)[1], accounts for ~20% of all breast tumours. Initially established as a prognostic biomarker, its greatest value today is as a predictor of trastuzumab benefit as well as other agents that target the HER2 pathway. Introduction of trastuzumab therapy markedly improved the poor prognosis associated with HER2+[2]. Subsequent identification of resistance mechanisms and the incorporation of new drugs with a better or different blockade of HER2 have improved survival outcome in the metastatic setting[3,4]. In early stages, incorporation of new anti-HER2 agents has provided discordant results. On one hand, locally advanced and large operable tumours showed dramatic increase in pathological complete rates (pCR) with the incorporation of lapatinib or pertuzumab to standard neoadjuvant trastuzumab and chemotherapy combination. With pCR validated as surrogate endpoint for disease-free survival (DFS) in patients with HER2+ disease[5], pertuzumab has granted approval by the European Medicines Agency (EMA) and the Food and Drug Administration (FDA) for this population. On the other hand, the addition of lapatinib to standard adjuvant trastuzumab and chemotherapy combination, provided statistically non-significant absolute benefit in the range of 2% at 4.5-years in DFS[6]. Results from a second large study incorporating pertuzumab to trastuzumab in the same setting are awaited. However, a constraint to clinically relevant achievements in this population is the low-modest risk following the high efficacy of trastuzumab and chemotherapy. Indeed, a single-arm treatment study in patients with predominantly stage I HER2+ breast cancer (i.e. T1 and node-negative or N1mic) exploring adjuvant low-intensity weekly paclitaxel for 12 weeks with 1 year of trastuzumab obtained a 3-year 98.7% DFS[7].

New strategies are needed in early HER2+ breast cancer to optimize and de-escalate treatments. In the HER2-negative/HR+ disease, gene expression-based assays have been incorporated to personalize risk and, most important, to establish the benefits and needs of adjuvant chemotherapy. The lack of any predictive tool in the HER2+ landscape is a question addressed for years that is penalizing adjuvant studies.

Three previous neoadjuvant studies have shown that ERBB2 mRNA expression alone is associated with a higher likelihood of pCR following chemotherapy and anti-HER2 therapy in patients with HER2+ disease[8-10]. In the NeoALTTO study[11], RNA sequencing of 254 baseline samples (of 455 patients included) was evaluated[8]. The NeoALTTO randomized 455 women with HER2+ early-stage breast cancer to trastuzumab, lapatinib, or the combination for 6 weeks followed by the addition of weekly paclitaxel for 12 weeks. After systemic treatment, patients underwent surgery[11]. The results revealed that high ERBB2 mRNA expression was associated with pCR in all treatment arms[8]. In another retrospective study from the NeoALTTO trial, HER2 protein expression-only was also found associated with a higher likelihood of pCR[12]. In the second clinical trial, the CALGB40601, patients with stage II to III HER2+ breast cancer were randomly assigned to chemotherapy (i.e. paclitaxel) plus trastuzumab alone or with the addition of lapatinib for 16 weeks before surgery[9]. Retrospective analysis revealed that high expression of ERBB2 by mRNA were associated with pCR in the entire population[9]. Finally, in the Tryphaena open-label phase II study, patients with operable, locally advanced, or inflammatory HER2+ breast cancer were randomized 1:1:1 to receive 6 neoadjuvant cycles of 3 different multi-agent chemotherapy regimens in combination with trastuzumab and pertuzumab[10]. Of the different molecular biomarkers analyzed, HER2 levels (protein and mRNA) showed an association with pCR rates when data from all arms were pooled.

The previous associations between baseline ERBB2 mRNA or protein with pCR following anti-HER2 therapy needs special consideration. Indeed, the 3 clinical trials (i.e. NeoALTTO, CALGB40601 and Tryphaena) included backbone chemotherapy in all their treatment arms. Thus, one cannot discriminate the predictive effect of ERBB2 expression over chemotherapy. In fact, a previous large study in the adjuvant setting observed a significant interaction between HER2-positivity (as defined standard criteria using IHC and/or FISH) and paclitaxel benefit[13]. In this study, 1,500 women with node-positive breast cancer who had been randomly assigned to receive doxorubicin (60, 75, or 90 mg per square meter of body-surface area) plus cyclophosphamide (600 mg per square meter) for four cycles, followed by four cycles of paclitaxel (175 mg per square meter) or observation. Tissue blocks from 1322 of these 1500 women were available[13]. Immunohistochemical analyses of these tissue specimens for HER2 with the CB11 monoclonal antibody against HER2 or with a polyclonal-antibody assay kit and fluorescence in situ hybridization for HER2 amplification were performed. The interaction between HER2 positivity and the addition of paclitaxel to the treatment was associated with a hazard ratio for recurrence of 0.59 (P=0.01)[13]. Patients with a HER2+ breast cancer benefited from paclitaxel, regardless of estrogen-receptor status, but paclitaxel did not benefit patients with HER2-negative, estrogen-receptor—positive cancers. Thus, one cannot exclude the possibility that high baseline levels of ERBB2 are also predictive of chemotherapy benefit, or predictive of a synergy effect between the two treatments (i.e. chemo and anti-HER2, single or double), something that NeoALTTO, CALGB40601 and Tryphaena cannot rule out because they did not include patients without chemotherapy. Moreover, none of these studies have evaluated the predictive value of the changes in ERBB2 mRNA expression following 2 weeks of treatment.

Given that the dual HER2 blockade improves the efficacy of single-agent HER2 therapy, a clinical question that arises is whether the dual blockade may eliminate the need for chemotherapy in a subset of patients. Exclusive dual HER2 blockade has shown high activity in a group of patients with metastatic and primary HER2+ breast cancer[14-16]. In HER2+ metastatic breast cancer previously treated with trastuzumab, the addition of pertuzumab or lapatinib to trastuzumab achieves higher clinical benefit than either pertuzumab or lapatinib alone[16]. In primary HER2+ breast cancer, chemotherapy-free neoadjuvant trastuzumab-lapatinib or trastuzumab-pertuzumab combinations achieved pCR rates in the breast of 17-27%[14,15]. Overall, results suggest that a subset of patients with HER2+ breast cancers is highly sensitive to dual anti HER2 blockade and could potentially be treated without cytotoxic therapy.

A major challenge today is to discover biomarkers that will identify the more sensitive patients to dual HER2 blockade without chemotherapy. To date, hormone receptor-positivity by immunohistochemistry (IHC) is the only molecular biomarker to predict response to dual HER2 blockade without chemotherapy. In the TBCRC006 trial, the pCR rate in estrogen receptor-positive disease was 21% versus 36% in ER-negative disease following 12 weeks of treatment with lapatinib and trastuzumab (and endocrine therapy if the tumour was ER+)[15]. In the NeoSphere trial, the pCR rate in estrogen receptor (ER)-positive or progesterone receptor (PR)-positive disease was 5.9% versus 27.3% in ER-negative or PR-negative disease following 12 weeks of treatment with pertuzumab and trastuzumab (Group C)[14]. However, this biomarker is not enough to identify those patients that will gain the highest benefit from dual HER2 blockade without chemotherapy. Currently, 30% of patients with HER2-positive (HER2+) breast cancer benefit substantially from dual HER2 blockade without chemotherapy. However, there is a need to identify these patients before and during treatment.

Nowadays, the combination of anti-HER2 doublets (either lapatinib+trastuzumab or pertuzumab+trastuzumab) with optimal multi-agent chemotherapy regimens are providing pCR rates in the range of ~60%[10], and pertuzumab has been specifically approved by the FDA and the EMA for patients with HER2+ early breast cancer with primary tumours>2 cm or node-positive disease. On the other hand, patients with stage I HER2+ disease, weekly paclitaxel for 12 doses plus single anti-HER2 (i.e. trastuzumab) is considered an acceptable regimen[7]. This treatment strategy provides pCR rates ranging from 29% to 46%[11].

Nowadays, in order to select the more appropriate therapy for the treatment of breast cancer is the hormone receptor status test, a test that tells whether or not the breast cancer cells have receptors for the hormones estrogen and progesterone. A cancer is called estrogen-receptor-positive (or ER+) if more than 1% of tumor cells express ER by IHC. This suggests that the cancer cells, like normal breast cells, may receive signals from estrogen that could promote their growth. The cancer is progesterone-receptor-positive (PR+) if more than 1% of tumor cells express ER by IHC. Hormone receptor status test by IHC, however, fails in providing an accurate information of the receptor, in some particular cases of breast cases, which, unfortunately, can cause a physician to take a wrong decision in deciding the more appropriate therapeutic protocol.

In spite of the efforts made, there is the need of biological markers that provide accurate predictive information of the success of a particular therapy prior its administration to the patient diagnosed of breast cancer.

SUMMARY OF INVENTION

The inventors have found that the ERBB2 gene product expression, in particular mRNA levels, when they are quantified in a patient already diagnosed of HER2+ breast cancer, and before receiving any therapy, can provide useful information about the positive or negative response to the administration of anti-HER2 therapy in the absence of chemotherapy (see FIG. 5).

From the data provided below, it is remarkable the fact that using ERBB2 as a biomarker, the information provided about the pathological complete response ("pCR") is substantially more accurate when compared with the protocol currently accepted by physicians, which is based on determining the hormone receptor status (see Table 4 below).

It is remarkable that the information provided by the ERBB2 biomarker, according to the present invention, is for a population of patients with HER2+ disease that might be candidates to receive anti-HER2 therapy and avoid chemotherapy. This is of great importance because, as it has been pointed out above, ERBB2 can affect the chemotherapy effectiveness and previous studies have not discriminated the effect of ERBB2 biomarker with chemotherapy versus anti-HER2 therapy.

Therefore, the invention means a great advance in accurately predicting, before starting the therapy, how a patient already diagnosed from HER2+ breast cancer could positively respond to anti-HER2 therapy without chemotherapy. This can be of great value for the physician in order to decide the best therapeutic strategy to successfully overcome the disease.

The first aspect of the invention refers to an in vitro method to determine the efficacy of an anti-HER2 therapy in the absence of chemotherapy in a patient with HER2+ breast cancer comprising the detection and/or quantification of a gene expression product of HER2 in an isolated test sample from the patient, before starting the anti-HER2 therapy.

In addition to the above, the present inventors have also found that determining the ratio of ERBB2 product gene expression before starting an anti-HER2 therapy and after a time of starting the therapy, it can also helps to predict the efficacy of anti-HER2 treatment in the absence of chemotherapy in a patient already diagnosed with HER2+ breast cancer.

As it is shown below, ERBB2 levels determined before and after 15 days of starting the anti-HER2 therapy in the absence of chemotherapy, predicts treatment efficacy compared with hormone receptor status (see Table 6 below). In addition to this, determining ERBB2 gene product expression levels between these two timepoints (i.e. before and after 15 days) during anti-HER2 therapy provides valuable information for deciding whether anti-HER2 treatment should be withdrawn.

Thus, a second aspect of the invention refers to an in vitro method to determine the efficacy of an anti-HER2 therapy in the absence of chemotherapy of a patient with HER2+ breast cancer comprising:

(a) the detection and/or quantification of a gene expression product of HER2 in an isolated biological sample of the patient:

(a.i) before starting the anti-HER2 therapy, and
(a.ii) after the initiation of the anti-HER2 therapy.

The results provided herein open the door to further studies in HER2+ breast cancer evaluating the long-term survival outcomes of chemotherapy-free dual HER2 blockade after selecting patients based on ERBB2 mRNA expression levels.

With the method of the second aspect of the invention, 64.9%-75.0% pCR rates were observed in the group of patients treated with dual HER2 blockade without chemotherapy with high baseline ERBB2 expression, or high ratio of ERBB2 expression between week 2 and baseline timepoints, suggesting that chemotherapy could be avoided in a subset of patients, which represents around ~25% (i.e. a quartile) of all HER2+ patients. These pCR rates are currently achieved with multi-agent chemotherapy in combination with dual HER2 blockade if no patient selection is taken into account.

A third aspect of the present invention refers to an in vitro method for deciding or recommending a patient with HER2+ breast cancer whether to initiate an alternative medical regime to an anti-HER2 therapy, that comprises:
  (a) the detection and/or quantification of a gene expression product of HER2 in an isolated biological sample of the patient:
    (a.i) before starting an anti-HER2 therapy in the absence of chemotherapy, and
    (a.ii) after the initiation of an anti-HER2 therapy in the absence of chemotherapy.

A fourth aspect of the present invention refers to the use of a gene expression product of HER2 as an in vitro marker for determining the efficacy of anti-HER2 therapy in the absence of chemotherapy in a patient with HER2+ breast cancer, or alternatively as an in vitro marker for deciding or recommending whether to initiate an alternative medical regime to anti-HER2 therapy in a patient with HER2+ breast cancer before receiving an anti-HER2 therapy without chemotherapy.

A fifth aspect of the present invention refers to the use of means for determining the presence or for quantifying the gene expression product of HER2 in the methods of the invention.

DETAILED DESCRIPTION OF THE INVENTION

Figure 1:
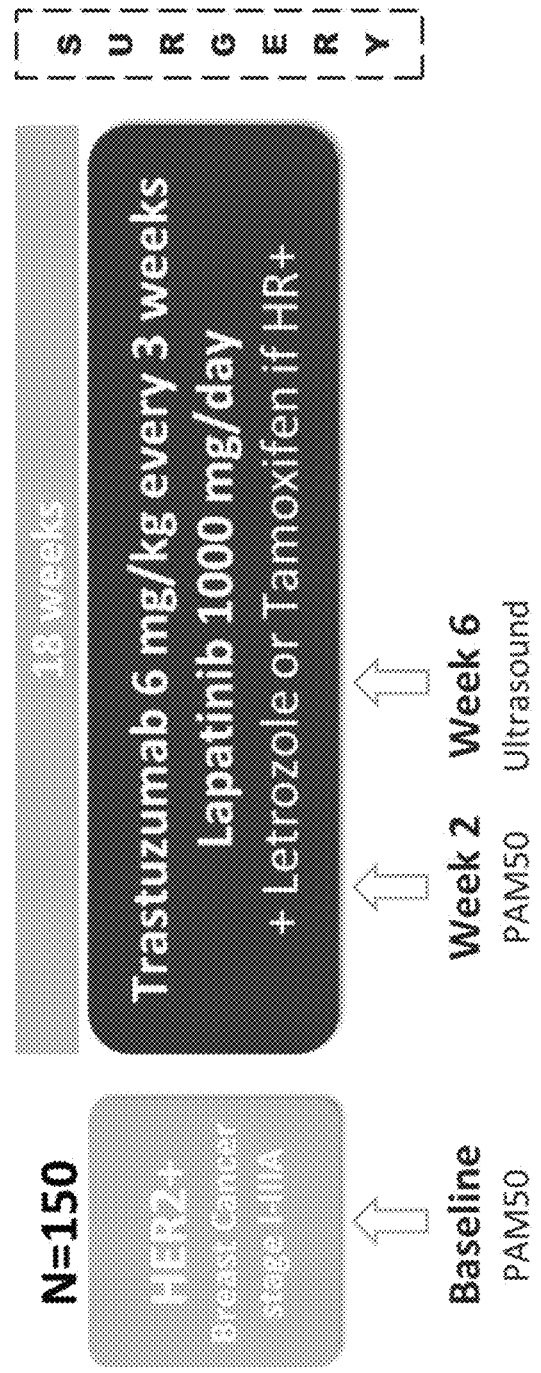
FIG. 1 PAMELA trial schema.

HER2 (HER2-positive) breast cancer is a breast cancer that tests positive for a protein called human epidermal growth factor receptor 2 (HER2). The techniques used by clinical practice to determine the expression of HER2 are well known by the expert in the field, for example by detecting the protein by immunohistochemistry or by detecting the number of copies by Fluorescence in situ Hybridization (FISH), SPoT-Light HER2 CISH test (Subtraction Probe Technology Chromogenic In Situ Hybridization) or by Inform HER2 Dual ISH test (Inform Dual In Situ Hybridization).

The gene "HER2" ("ERBB2", v-erb-b2 avian erythroblastic leukemia viral oncogene homolog 2) (GeneID: 64) encodes a member of the epidermal growth factor (EGF) receptor family of receptor tyrosine kinases. Amplification and/or overexpression of this gene has been reported in numerous cancers, including breast and ovarian tumors. Gene synonyms are the following CD340; HER-2; HER-2/neu; HER2; MLN 19; NEU; NGL; and TKR1.

SEQ ID NO: 1 (ERBB2) (NM_001005862.1, date of Jan. 19, 2014) corresponds to the complementary DNA (cDNA) that codifies for the mRNA of the Homo sapiens variant 2.

Alternative splicing results in several additional transcript variants, some encoding different isoforms. Allelic variations at amino acid positions have been reported.

The HER2 protein ID is the following: "NP_001005862.1" (SEQ ID NO: 2).

The target sequence of ERBB2 for the detection and/or quantification in a preferred embodiment is SEQ ID NO: 3

(ACAGACACGTTTGAGTCCATGCCCAATCCCGAGGGCCGGTATACATTCG

GCGCCAGCTGTGTGACTGCCTGTCCCTACAACTACCTTTCTACGGACGTG

G).

In the present invention, the detection and/or quantification of a gene expression product of HER2 has been performed in patients with HER2+ breast cancer before and during anti-HER2 therapies in the absence of chemotherapy.

Therefore, in a preferred embodiment of the methods of the invention the patient in addition has not received any chemotherapy before the detection and/or quantification of the gene expression product of HER2.

In one embodiment of the first aspect of the invention, when the gene expression product of HER2 is overexpressed it is indicative of anti-HER2 efficacy in the absence of chemotherapy. The overexpression is in relation to a reference sample, the reference sample is a normal breast tissue of a healthy person.

In one embodiment of the first aspect of the invention, when the amount of gene expression product of HER2 is highly expressed (defined, for example, as the top 25% percentile, or a ERBB2 gene expression score of ≥3.22), it is indicative of high anti-HER2 efficacy in the absence of chemotherapy.

In the present invention the term "gene expression product" refers to the messenger ribonucleic acid (messenger RNA or mRNA) or the protein.

In one embodiment, the gene expression product is mRNA. By "mRNA" it is encompassed both the whole mRNA sequence as well as fragments thereof.

In another embodiment, the term "gene expression product" refers to HER2 protein. By "HER2 protein" it is encompassed both the whole HER2 protein of sequence SEQ ID NO: 2, as well as functional fragments thereof (such as immunological fragments thereof) or a protein with a sequence having a percentage of identity of at least 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 percent sequence identity, preferably 100% identity with SEQ ID NO: 2.

In the present invention the term "identity" refers to the percentage of residues that are identical in the two sequences when the sequences are optimally aligned. If, in the optimal alignment, a position in a first sequence is occupied by the same amino acid residue as the corresponding position in the second sequence, the sequences exhibit identity with respect to that position. The level of identity between two sequences (or "percent sequence identity") is measured as a ratio of the number of identical positions shared by the sequences with respect to the size of the sequences (i.e., percent sequence identity=[number of identical positions/total number of positions]×100).

A number of mathematical algorithms for rapidly obtaining the optimal alignment and calculating identity between two or more sequences are known and incorporated into a number of available software programs. Examples of such programs include the MATCH-BOX, MULTAIN, GCG, FASTA, and ROBUST programs for amino acid sequence analysis, among others. Preferred software analysis programs include the ALIGN, CLUSTAL W, and BLAST programs (e.g., BLAST 2.1, BL2SEQ, and later versions thereof).

For amino acid sequence analysis, a weight matrix, such as the BLOSUM matrixes (e.g., the BLOSUM45, BLOSUM50, BLOSUM62, and BLOSUM80 matrixes), Gonnet matrixes, or PAM matrixes (e.g., the PAM30, PAM70, PAM120, PAM160, PAM250, and PAM350 matrixes), are used in determining identity.

The BLAST programs provide analysis of at least two amino acid sequences, either by aligning a selected sequence against multiple sequences in a database (e.g., GenSeq), or, with BL2SEQ, between two selected sequences. BLAST programs are preferably modified by low complexity filtering programs such as the DUST or SEG programs, which are preferably integrated into the BLAST program operations. If gap existence costs (or gap scores) are used, the gap existence cost preferably is set between about −5 and −15. Similar gap parameters can be used with other programs as appropriate. The BLAST programs and principles underlying them are further described in, e.g., Altschul et al., "Basic local alignment search tool", 1990, J. Mol. Biol, v. 215, pages 403-410.

For multiple sequence analysis, the CLUSTAL W program can be used. The CLUSTAL W program desirably is run using "dynamic" (versus "fast") settings. Amino acid sequences are evaluated using a variable set of BLOSUM matrixes depending on the level of identity between the sequences. The CLUSTAL W program and underlying principles of operation are further described in, e.g., Higgins et al., "CLUSTAL V: improved software for multiple sequence alignment", 1992, CABIOS, 8(2), pages 189-191.

In an embodiment of the present invention, optionally in combination with any of the embodiments provided above or below, the gene expression product is mRNA (messenger RNA) (in a preferred embodiment is SEQ ID NO: 1). In another embodiment, the sequence detected and/or quantified is SEQ ID NO: 3.

In a preferred embodiment of the present invention the product of expression of HER2 is quantified. In a more preferred embodiment the mRNA of HER2 is quantified. In a more preferred embodiment SEQ ID NO: 1 is quantified.

In a preferred embodiment of the present invention the product of expression of HER2 quantified by an amplification technique.

In a more preferred embodiment of the present invention the mRNA of HER2 is quantified using specific primers and/or probes.

The expert in the field knows that adding additional steps to detection techniques quantification can be achieved.

Detection and/or quantification can be performed by any method known to the skilled person, provided that said method permits the detection or quantification of mRNA in a biological sample. Included among the examples of these procedures are PCR, quantitative real-time PCR (QPCR), multiplex PCR, NASBA, LCR, RT-PCR, RNA sequencing, array hybridization or "Northern" transfer, or combinations of these. In a preferred embodiment, the determination of the mRNA is performed by the nCounter platform (Nanostring Technologies). In most procedures, the use of primers and/or probes are required to detect and/or quantify the mRNA of interest. A skilled person would get easily and directly the sequence of the primers and or probes that can be used from the sequence of the mRNA of HER2.

In most methods of detection and quantification of RNA mentioned above, before performing this procedure it is necessary to convert the RNA to complementary DNA (cDNA). This conversion is accomplished by known techniques by skilled in the art, such as reverse transcription, among others.

In one embodiment of any of the methods provided by the present invention, the detection and/or quantification of the gene expression product of HER2 after the initiation of an anti-HER2 therapy is performed at a day from the $5^{th}$ to the $20^{th}$ day (5, 6, 7, 8, 9, 10, 11, 12, 13, 14, 15, 16, 17, 18, 19 or 20) after the initiation of the anti-HER2 therapy. In another embodiment, the detection and/or quantification of the gene expression product of HER2 after the initiation of an anti-HER2 therapy is performed at a day from the $5^{th}$ to the $19^{th}$ day, more preferably from the $10^{th}$ to the $16^{th}$ day. In another embodiment, the detection and/or quantification of the gene expression product of HER2 after the initiation of an anti-HER2 therapy is performed at day $14^{th}$ after the initiation of the anti-HER2 therapy.

In a preferred embodiment of the methods of the invention the gene expression product of HER2 is mRNA and it is quantified by at least a pair of primers and/or probes. In a preferred embodiment of the present invention the probe detects SEQ ID NO: 3, in a particular embodiment two probes detect SEQ ID NO: 3.

In the present invention the pathological complete response (pCR) is the absence of invasive neoplastic cells at microscopic examination of the primary tumour at surgery after a treatment HER2+ breast cancer by, preferably a dual HER2 blockade, more preferably with lapatinib and trastuzumab, has been completed.

In the present invention the term "after initiation of an anti-HER2 therapy" means that the subject has already received the treatment or that is receiving said treatment (ongoing treatment).

The anti-HER2 therapy in the present invention is not given in combination with chemotherapy. Therefore the anti-HER2 therapy is given to the patient in the absence of chemotherapy (without chemotherapy).

Known anti-HER2 therapies (treatment) include trastuzumab (Herceptin®), lapatinib (Tykerb®), neratinib (HKI-272), pertuzumab (Perjeta®) and ado-trastuzumab emtansine (Kadcyla®). In one embodiment of the in vitro methods provided by the present invention, the anti-HER2 therapy is selected from the list consisting of: trastuzumab, lapatinib, neratinib, pertuzumab and/or ado-trastuzumab emtansine, or any combinations thereof. Preferably is trastuzumab and lapatinib.

Therefore, in the case the patient receives trastuzumab and lapatinib, the method determines that said medical regime is effective when the gene expression of HER2, preferably by quantifying and/or detecting the mRNA, after the initiation of said therapy is decreased in comparison to the basal expression (before receiving said therapy). Thus, the treatment outcome of said patient is good. On the contrary, when said comparison shows that there is not a decrease in gene expression, then said medical regime is less effective or ineffective. Thus the treatment outcome of said patient is bad. In that case, the method of the present invention is useful for deciding or recommending to change said medical regime and in particular to initiate another treatment, and therefore is useful for determining the best therapeutic regime for a given patient with HER2+ breast cancer.

Chemotherapy (cytotoxic therapy) that could be used as said medical regime would be paclitaxel, docetaxel, carboplatin, doxorubicin, epirubicin, nab-paclitaxel, vinorelbine, capecitabine and eribulin.

In the present invention the term "efficacy" is related to the pCR of the HER2+ breast cancer, therefore the absence of invasive neoplastic cells at microscopic examination of the primary tumour at surgery is indicative that the treatment has been effective.

In a preferred embodiment of the invention the efficacy is pCR.

The efficacy can also be observed as any decrease in tumor size wherein imaging techniques are used.

The term "biological sample" includes, without being limited thereto, biological tissues and/or fluids from an individual, obtained by any method designed for that purpose known to persons skilled in the art. The biological sample comprises the product of expression of the gene that codifies for HER2.

In an embodiment of the in vitro methods provided by the present invention the sample is a breast tissue, blood, serum or plasma. In a preferred embodiment is a biopsy sample from breast cancer tissue. In the present invention, the biological sample is fresh, frozen, fixed or fixed and embedded in paraffin. In a preferred embodiment, the sample is a breast cancer tissue fixed and embedded in paraffin. The biological sample can be collected by any means known by the expert in the field, for example by needle biopsy of the breast.

In the present invention the terms "patient", "subject" and "individual" are used interchangeably.

In the present invention the patient is a mammal, such as a mouse, rat, guinea pig, rabbit, dog, cat, bovine, horse, goat, sheep, primate or human, preferably is a human, more preferably is a woman. The patient can be of any age, gender or race.

In another preferred embodiment of the first, second, and third in vitro methods of the present invention the patient is a woman.

In the present invention, the patient has not received any previous cancer therapy (nor chemotherapy) before the initiation of the anti-HER2 therapy.

In another preferred embodiment of the in vitro methods of the present invention the anti-HER2 therapy is combined with endocrine therapy in hormone receptor-positive (HR+) patients.

The patient can be also a hormone receptor-negative (HR−) patient.

Endocrine therapy known by the expert in the field is for example: selective estrogen-receptor response modulators (SERMs) (for example tamoxifen or toremifene), aromatase inhibitors (for example anastrozole, exemestane, letrozole), estrogen-receptor downregulators (ERDs) (for example fulvestrant) and luteinizing hormone-releasing hormone agents (LHRHs) (for example goserelin, leuprolide and Triptorelin). In a preferred embodiment of the methods and uses of the present invention the endocrine therapy is selected form list consisting of: a selective estrogen-receptor response modulator, an aromatase inhibitor, an estrogen-receptor downregulators (ERDs) and/or a luteinizing hormone-releasing hormone agent, or any combination thereof. In a more preferred embodiment the endocrine therapy is selected form the list consisting of: tamoxifen, toremifene, anastrozole, exemestane, letrozole, fulvestrant, goserelin, leuprolide and/or Triptorelin, or any combinations thereof. In a more preferred embodiment, is letrozole or tamoxifen.

Thus a preferred embodiment of the methods of the invention refers to a method wherein the anti-HER2 therapy is trastuzumab and lapatinib. In a more preferred embodiment the patient in addition has not received chemotherapy. In a more preferred embodiment the gene expression product of HER2 is mRNA, in a preferred embodiment is SEQ ID NO: 1. In a preferred embodiment the patient is a HR− patient. In another preferred embodiment the patient is a HR+ patient, and the HER2-therapy is combined with letrozole or tamoxifen. In relation to the methods of the second and third aspect of the invention, in addition in a preferred embodiment the detection and/or quantification of the mRNA after the initiation of an anti-HER2 therapy in absence of chemotherapy is performed at day 14 after the initiation of the anti-HER2 therapy.

Thus a preferred embodiment of the methods of the invention refers to a method wherein the anti-HER2 therapy is trastuzumab and lapatinib; the patient is a HR− patient; the gene expression product of HER2 is mRNA, and in a preferred embodiment is SEQ ID NO: 1. In relation to the methods of the second and third aspect of the invention, in addition in a preferred embodiment the detection and/or quantification of the mRNA after the initiation of an anti-HER2 therapy in absence of chemotherapy is performed at day 14 after the initiation of the anti-HER2 therapy. In a preferred embodiment in addition the patient has not received chemotherapy previously to the HER2 detection/quantification.

In a preferred embodiment of the methods of the invention refers to a method wherein the anti-HER2 therapy is trastuzumab and lapatinib; the patient is a HR+ patient; the HER2-therapy is combined with letrozole or tamoxifen; the gene expression product of HER2 is mRNA, and in a preferred embodiment is SEQ ID NO: 1. In relation to the methods of the second and third aspect of the invention, in addition in a preferred embodiment the detection and/or quantification of the mRNA after the initiation of an anti-HER2 therapy in absence of chemotherapy is performed at day 14 after the initiation of the anti-HER2 therapy. In a preferred embodiment in addition the patient has not received chemotherapy previously to the HER2 detection/quantification.

Thus a preferred embodiment of the third aspect of the invention the anti-HER2 therapy is trastuzumab and lapatinib; the patient is a HR− patient; the gene expression product of HER2 is mRNA, and in a more preferred embodiment is SEQ ID NO: 1; the detection and/or quantification of the mRNA after the initiation of an anti-HER2 therapy in absence of chemotherapy is performed at day 14 after the initiation of the anti-HER2 therapy; and the alternative regime is chemotherapy. In a preferred embodiment in addition the patient has not received chemotherapy previously to the HER2 detection/quantification.

In a preferred embodiment of the third aspect of the invention the anti-HER2 therapy is trastuzumab and lapatinib; the patient is a HR+ patient; the HER2-therapy is combined with letrozole or tamoxifen; the gene expression product of HER2 is mRNA, in a more preferred embodiment is SEQ ID NO: 1; the detection and/or quantification of the mRNA after the initiation of an anti-HER2 therapy in absence of chemotherapy is performed at day 14 after the initiation of the anti-HER2 therapy; and the alternative regime is chemotherapy. In a preferred embodiment in addition the patient has not received chemotherapy previously to the HER2 detection/quantification.

In a preferred embodiment of the of the in vitro methods of the present invention, the method also comprises imaging the subject for breast cancer, for example by ultrasound. The imaging can be performed in any order in the method of the invention, therefore, before detecting and/or measuring the gene expression product of HER2. The reduction of cancer size is associated with efficacy of the HER2-therapy.

The present invention also refers to a method for determining efficacy and treatment of HER2+ breast cancer in a subject diagnosed with the disease, said method comprising the steps of:
  a) obtaining a first sample comprising a breast cancer tissue biopsy sample from the subject before the beginning of an anti-HER2 therapy;
  b) contacting the first sample with a first reagent, preferably a probe, that binds to the mRNA of HER2;
  c) measuring an amount of mRNA of HER2 that is bound to the first reagent in the first sample;
  d) comparing the amount of mRNA of HER2 bound to the first reagent in step c) with the mRNA of HER2 obtained from a second sample comprising a breast cancer tissue biopsy sample from the subject after the initiation of an anti-HER2 therapy;
  e) determining the treatment outcome for the subject and treating the subject, wherein:
    (i) if the amount of mRNA of HER2 bound to the first reagent in step c) is higher than the one of mRNA of HER2 value on the second sample, the anti-HER2 treatment is more or highly effective; and
    (ii) if the amount of mRNA bound to the first reagent in step c) is lower than the one of the mRNA of HER2 value on the second sample, the anti-HER2 treatment is less effective or ineffective, and the treatment is selected from the group consisting of: breast cancer removal, follow-up, chemotherapy, radiotherapy, and combinations thereof.

In an embodiment of the fourth aspect of the present invention, the gene expression product of HER2 is mRNA. More preferably wherein the gene expression product is SEQ ID NO: 1.

A preferred embodiment of the fourth aspect of the present invention is referred to the use wherein the gene expression product is the protein, in a preferred embodiment is SEQ ID NO: 2.

A preferred embodiment of the fourth aspect of the present invention is referred to the use wherein the anti-HER2 therapy is selected from the group consisting of: trastuzumab, lapatinib, neratinib, pertuzumab, ado-trastuzumab emtansine, or a combination thereof, preferably is trastuzumab and lapatinib.

In preferred embodiment of the fourth aspect of the present invention the patient is a woman, preferably is a hormone receptor-positive (HR+) patient. The patient is a HR+ patient or a receptor-negative (HR−) patient. Wherein the patient is a HR+ patient, the anti-HER2 therapy can be combined with endocrine therapy. In a more preferred embodiment the endocrine therapy is selected form the list consisting of: tamoxifen, toremifene, anastrozole, exemestane, letrozole, fulvestrant, goserelin, leuprolide and/or Triptorelin, or any combinations thereof. In a more preferred embodiment, is letrozole or tamoxifen.

In a preferred embodiment of the fourth aspect of the present invention the anti-HER2 therapy is trastuzumab and lapatinib; the patient is a HR− patient; the gene expression product of HER2 is mRNA, and in a preferred embodiment is SEQ ID NO: 1. In a preferred embodiment in addition the patient has not received chemotherapy previously to the HER2 detection/quantification.

In a preferred embodiment of the fourth aspect of the present invention the anti-HER2 therapy is trastuzumab and lapatinib; the patient is a HR+ patient; the HER2-therapy is combined with letrozole or tamoxifen; the gene expression product of HER2 is mRNA, and in a preferred embodiment is SEQ ID NO: 1. In a preferred embodiment in addition the patient has not received chemotherapy previously to the HER2 detection/quantification.

In a preferred embodiment of the fifth aspect of the present invention the gene expression product is mRNA, preferably SEQ ID NO: 1; or protein, preferably SEQ ID NO: 2.

In a preferred embodiment of the fifth aspect of the present invention the means form part of a kit.

Another aspect of the present invention is referred to a kit that comprises the specific means to detect the presence or absence of or quantify a gene expression product of HER2, preferably its mRNA, for use in the methods of the present invention. In a particular embodiment the kit comprises specific primers and/or probes, antibodies, or combinations thereof. In a particular embodiment the kit comprises specific primers and/or probes for detecting and/or quantifying SEQ ID NO: 1, in a more particular embodiment for detecting and/or quantifying SEQ ID NO: 3.

Throughout the description and claims the word "comprise" and variations of the word, are not intended to exclude other technical features, additives, components, or steps. Furthermore, the word "comprise" encompasses the case of "consisting of". Additional objects, advantages and features of the invention will become apparent to those skilled in the art upon examination of the description or may be learned by practice of the invention. The following examples and drawings are provided by way of illustration, and they are not intended to be limiting of the present invention. Reference signs related to drawings and placed in parentheses in

EXAMPLES

Example 1

ERBB2 as a Predictor of Response of Dual HER2 Blockade in the Absence of Cytotoxic Therapy Material and Methods:

Study Design and Patients:

PAMELA (NCT01973660) is a nonrandomised, multicentre, prospective, open-label phase 2 study in women with HER2+ breast cancer (FIG. 1). All eligible patients had centrally confirmed HER2, centrally performed estrogen receptor and progesterone receptor by immunohistochemistry, stage I-IIIA breast cancer with primary tumours larger than 1 cm in diameter, were aged 18 years or older, and had not received any previous cancer therapy. Tumours had to be HER2 immunohistochemistry 3+ or 2+ and positive for chromogenic in-situ hybridisation. Of note, HER2, ER, and PR testing were done under ISO15189 accreditation.

Other main inclusion criteria were: baseline Eastern Cooperative Oncology Group (ECOG) performance status of 0-2, baseline left ventricular ejection fraction (LVEF) of 50% or more, as measured by echocardiography or multiple gated acquisition (MUGA). Key exclusion criteria were multicentric tumours, inoperable stage III disease, stage IV disease, bilateral breast cancer, other malignancies, inadequate bone marrow or renal function, impaired liver function, impaired cardiac function, uncontrolled hypertension, pregnancy, and refusal to use contraception.

The study was undertaken in accordance with Good Clinical Practice guidelines and the World Medical Association Declaration of Helsinki. All patients provided written informed consent. Approvals for the study protocol were obtained from independent ethics committees.

Procedures:

Lapatinib was given orally at a daily dose of 1000 mg. Trastuzumab was given IV every 3 weeks at a loading dose of 8 mg/kg, followed by 6 mg/kg. Patients with HR+ received letrozole (2.5 mg daily) or tamoxifen (20 mg daily) according to menopausal status. The total duration of treatment was 18 weeks. At week 2, a core-needle biopsy was mandatory. At week 6, an early response evaluation by ultrasound was mandatory. Any increase in tumour size during the study or at week 6 was considered a treatment failure, and the patient would be categorized as not sensitive for the primary endpoint (i.e. pCR with dual blockade). These patients were treated with trastuzumab and weekly paclitaxel 80 mg/m2 for 12 doses and lapatinib 750 mg orally. Surgery was performed between 1 and 3 weeks after the last dose of dual HER2 blockade, or 2 and 3 weeks after the last dose of paclitaxel. Standard adjuvant chemotherapy was administered according to the physician's discretion.

Gene Expression Analysis:

A section of the formalin-fixed paraffin-embedded (FFPE) breast tissue was first examined with haematoxylin and eosin staining to confirm presence of invasive tumour cells (≥10%) and determine the minimum tumour surface area (>4 mm2). Patients could not be recruited unless the minimum tissue requirement for gene expression analysis was met. For samples at day—15, those without invasive tumour cells were also profiled. For RNA purification (Roche® High Pure FFPET RNA isolation kit), ≥1-5 10 µm FFPE slides were used for each tumour specimen, and macrodissection was performed, when needed, to avoid normal contamination. A minimum of ~100 ng of total RNA was used to measure the expression of the 555 breast cancer-selected genes and 5 housekeeping genes (ACTB, MRPL19, PSMC4, RPLP0, and SF3A1) using the nCounter platform (Nanostring Technologies, Seattle, WA, US). Data were log base 2 transformed. The geometric mean of the 5 housekeeping genes was obtained for each sample, and was used as a normalization factor for each gene in each sample. The design of the 560-CodeSet, including the target sequences, can be found in table 8.

Statistical Analysis:

The primary endpoint was pCR in the breast, which is defined as the absence of invasive neoplastic cells at microscopic examination of the primary tumour at surgery. Remaining in situ lesions were allowed.

Figure 2:
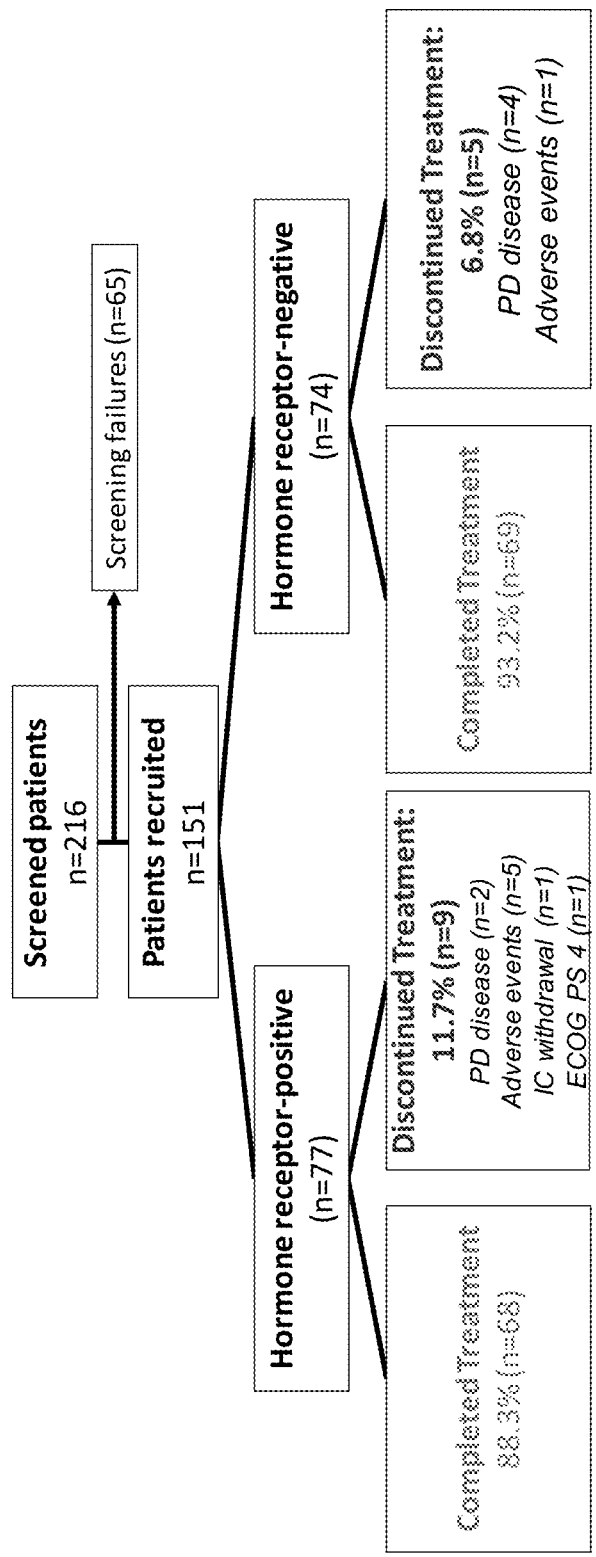
FIG. 2 shows the diagram that resumes the patient information of the PAMELA trial.

Results:

The PAMELA Clinical Trial:

From October 2013 to December 2015, 151 patients were recruited across 19 sites in Spain. Of 151 recruited patients, 137 patients completed treatment as planned and 14 patients discontinued treatment (FIG. 2). The baseline median tumour size by clinical breast examination was 2.4 cm, and most patients had negative axilla (64.9%) and were post-menopausal (59.6%) (Table 1). Among patients with HR+ disease (n=77), 52% and 48% received tamoxifen and letrozole respectively, accordingly with menopausal status. All patients who underwent surgery had a valid assessment of pathological response.

TABLE 1

Patient demographics at baseline.

| | N | % |
|---|---|---|
| N | 151 | — |
| Age, mean (range) | | 55 (29-86) |
| Tumor size (mm), median (range) | | 24 (10-110) |
| Clinical nodal status | | |
| N0 | 98 | 64.9% |
| N1 | 50 | 33.1% |
| N2 | 3 | 2.0% |
| Hormone receptor (HR) status | | |
| Negative | 74 | 49.0% |
| Positive | 77 | 51.0% |
| Letrozole | 37 | 48.0% |
| Tamoxifen | 40 | 52.0% |
| Menopausal status | | |
| Pre-menopausal | 61 | 40.4% |
| Post-menopausal | 90 | 59.6% |
| Tumor stage | | |
| T1 | 60 | 39.7% |
| T2 | 79 | 52.3% |
| T3 | 12 | 8.0% |

A pCR in the breast was noted in 46 of 151 women (30.5%, 95% CI 23.4-38.5). Consistent with previous findings, fewer pCRs were noted in tumours that were HR+ compared to those HR-negative (18.2% vs 43.2%; p=0.001). Among 14 patients who discontinued treatment, 6 had treatment failure (4.0% of all patients). Treatment failure occurred in HR+ (n=2) and HR-negative (n=4) disease. Five patients out of 6 with treatment failure received neoadjuvant paclitaxel, lapatinib and trastuzumab as per protocol and none achieved a pCR.

Among the different clinical-pathological variables evaluated (age, tumour size, tumour stage, menopausal status, nodal status and hormone receptor [HR] status), only HR status was found significantly associated with pCR (Table 2).

TABLE 2

Logistic regression model analyses of treatment pathological response.

| Signatures | N | in-breast pCR rate | OR | Lower 95% | Upper 95% | p-value |
|---|---|---|---|---|---|---|
| Age (cont. variable) | — | — | 1 | 0.97 | 1.02 | 0.862 |
| Tumour size (cont. variable) | — | — | 0.98 | 0.96 | 1.01 | 0.213 |
| Tumour stage | | | | | | |
| T1 | 60 | 30.0% | 1 | — | — | — |
| T2 | 79 | 32.9% | 1.14 | 0.56 | 2.38 | 0.71 |
| T3 | 12 | 16.7% | 0.47 | 0.1 | 2.0 | 0.35 |
| Menopausal status | | | | | | |
| Pre | 61 | 33.3% | 1 | — | — | — |
| Post | 90 | 28.6% | 0.83 | 0.41 | 1.69 | 0.61 |
| Nodal status | | | | | | |
| 0 | 98 | 347% | 1 | — | — | — |
| 1-2 | 53 | 22.6% | 0.55 | 0.26 | 1.19 | 0.127 |
| RH status | | | | | | |
| HR+ | 77 | 18.2% | 1 | — | — | — |
| HR-negative | 74 | 43.2% | 3.42 | 1.64 | 7.2 | 0.001 |

*OR, odds ratio.

Figure 3:
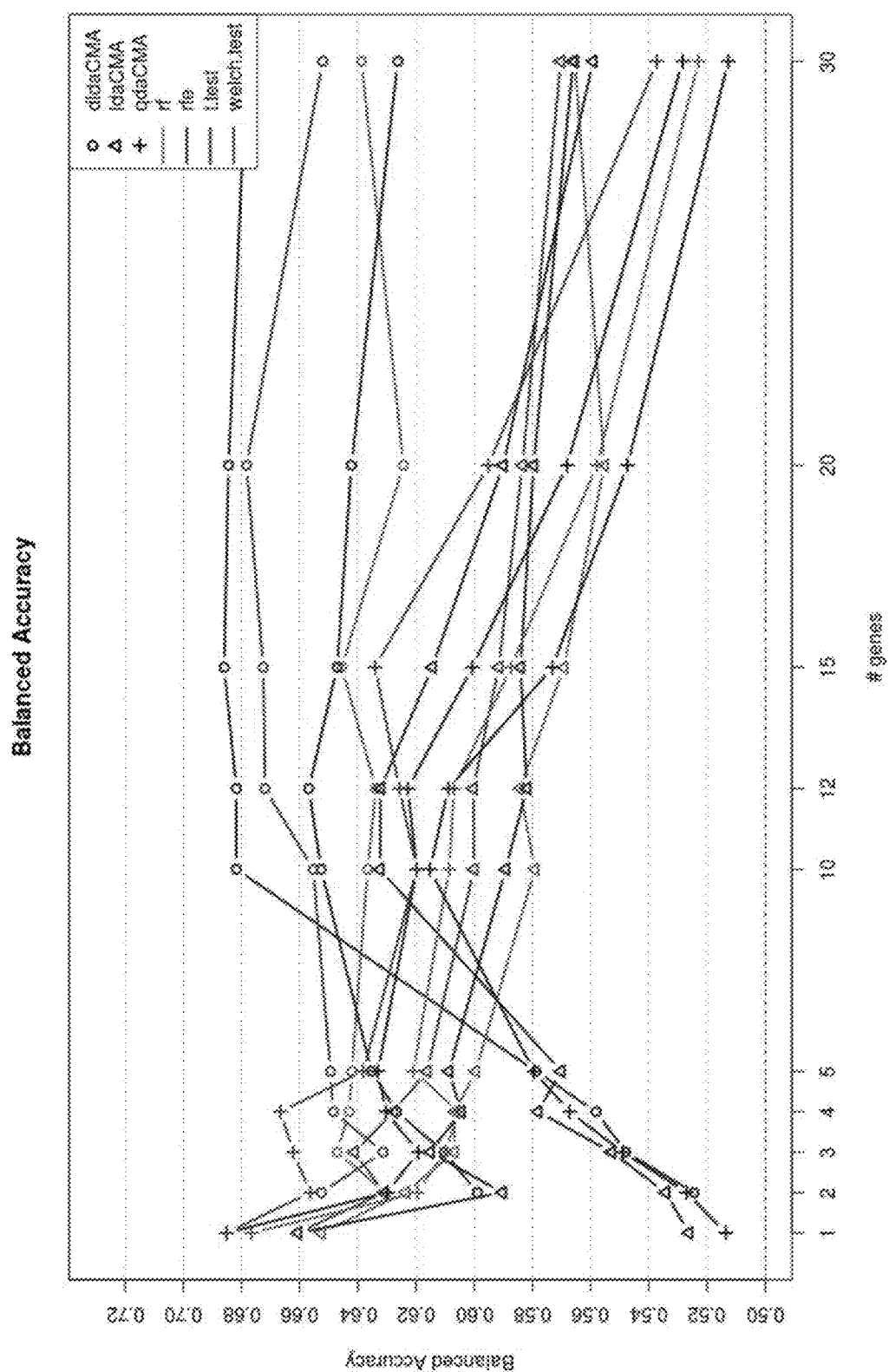
FIG. 3 describes the balanced accuracy analyses using variable number of genes (measured at baseline) and different methods of classification and variable selection. dlda, diagonal linear discriminant analysis; lda, linear discriminant analysis; qda, quadratic discriminant analysis; rf, random forests; rfe, recursive feature elimination; t.test, Student's t-test; welch.test, Welch's t-test.

Prediction of pCR with Gene Expression from Baseline Samples:

Expression of 555 breast cancer-related genes and 5 house-keeping genes was performed successfully in all baseline samples (n=151) (see table 8). Cross validation analyses (10-fold, repeated 25 times) using 4 methods of variable selection (t-test, Welch's t-test, random forests [rf] and recursive feature elimination [rfe]), different number of selected genes (1, 2, 3, 4, 5, 10, 12, 15, 20 and 30) and 3 classification methods (diagonal linear discriminant analysis [dlda], linear discriminant analysis [lda] and quadratic discriminant analysis [qda]) were performed to select the best model. As shown in FIG. 3 and Table 3, the best 'balanced accuracy', a measure of classification performance, was obtained with a single gene, which was ERBB2 in all the analyses performed.

TABLE 3

Genes selected during 10-fold cross-validation using different methods of classification and gene selection.

| Class. method | Variable Selection Method | N | Gene | Mis-class. | sensi-tivity | speci-ficity | Balanced accuracy |
|---|---|---|---|---|---|---|---|
| QDA | t.test | 1 | ERBB2 | 24.4% | 51.4% | 86.2% | 68.8% |
| QDA9 | welch.test | 1 | ERBB2 | 24.4% | 51.4% | 86.2% | 68.8% |
| DLDA14 | welch.test | 20 | — | 34.3% | 71.8% | 63.1% | 67.4% |
| DLDA13 | welch.test | 12 | — | 34.2% | 70.3% | 63.8% | 67.1% |
| LDA | t.test | 1 | ERBB2 | 24.0% | 42.7% | 90.6% | 66.7% |
| LDA9 | welch.test | 1 | ERBB2 | 24.0% | 42.7% | 90.6% | 66.7% |
| DLDA19 | rfe | 10 | — | 30.1% | 57.2% | 75.5% | 66.3% |
| DLDA12 | welch.test | 10 | — | 34.5% | 68.0% | 64.4% | 66.2% |
| DLDA11 | welch.test | 5 | — | 33.1% | 64.3% | 68.1% | 66.2% |
| DLDA5 | t.test | 10 | — | 34.7% | 66.6% | 64.7% | 65.6% |
| DLDA9 | welch.test | 3 | — | 31.2% | 56.7% | 74.0% | 65.4% |
| QDA10 | welch.test | 2 | — | 31.1% | 55.9% | 74.6% | 65.3% |

Figure 4:
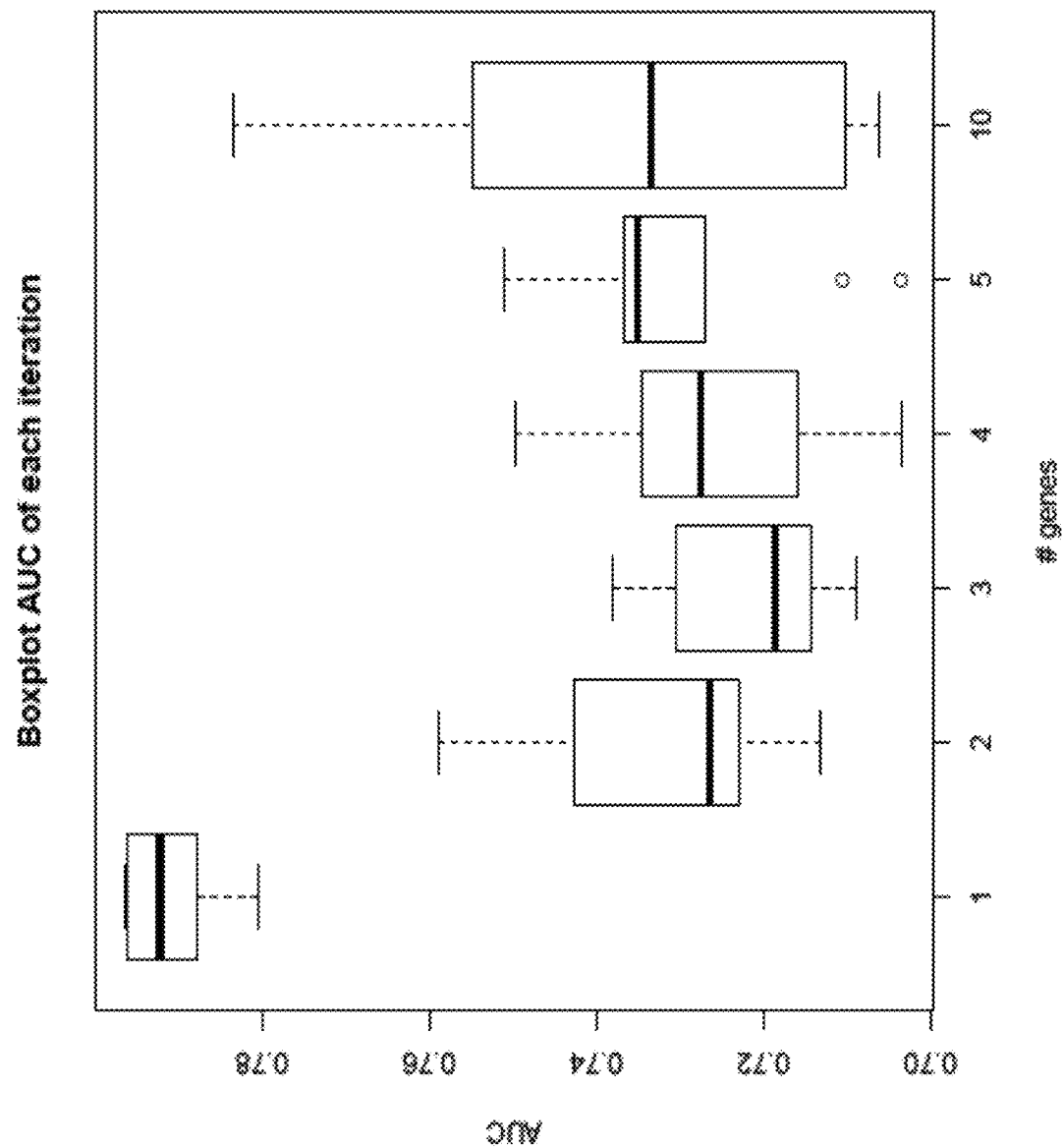
FIG. 4 shows the cross-validation area under the curve (AUC) analyses using baseline samples-only after selection of 1, 2, 3, 4, 5 and 10 genes.

"Class. Method": Classification method;
N: "Number of genes selected";
"Misclass.": Misclassification Next, it was evaluated, using cross-validation analyses (10-fold, repeated 25 times) and the qda method, the prediction performance using Receiver Operating Characteristic (ROC) analysis (i.e. area under the ROC [auROC]curve) when 1, 2, 3, 4, 5 and 10 genes were selected. As shown in FIG. 4, 1 single gene, which was ERBB2 in all cases, showed the highest auROCs.

Figure 5A:
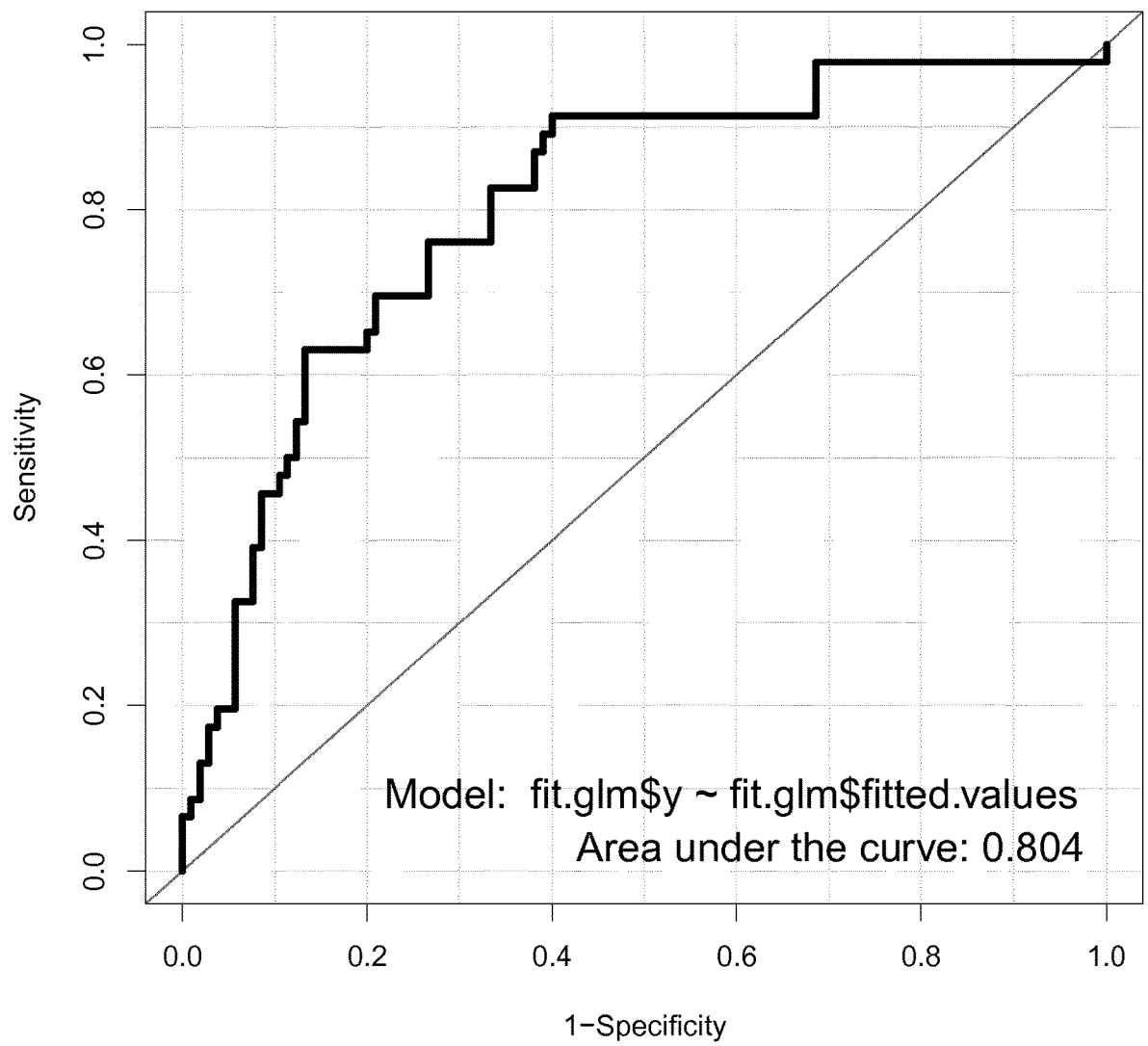
FIG. 5 describes the association of ERBB2 expression with pCR in the entire dataset of baseline samples (n=151). A, cross-validation area under the curve (AUC) analysis; B; box-whisker plot of ERBB2 expression in patients that achieved a pCR versus those that did not (non-pCR).
Figure 5B:
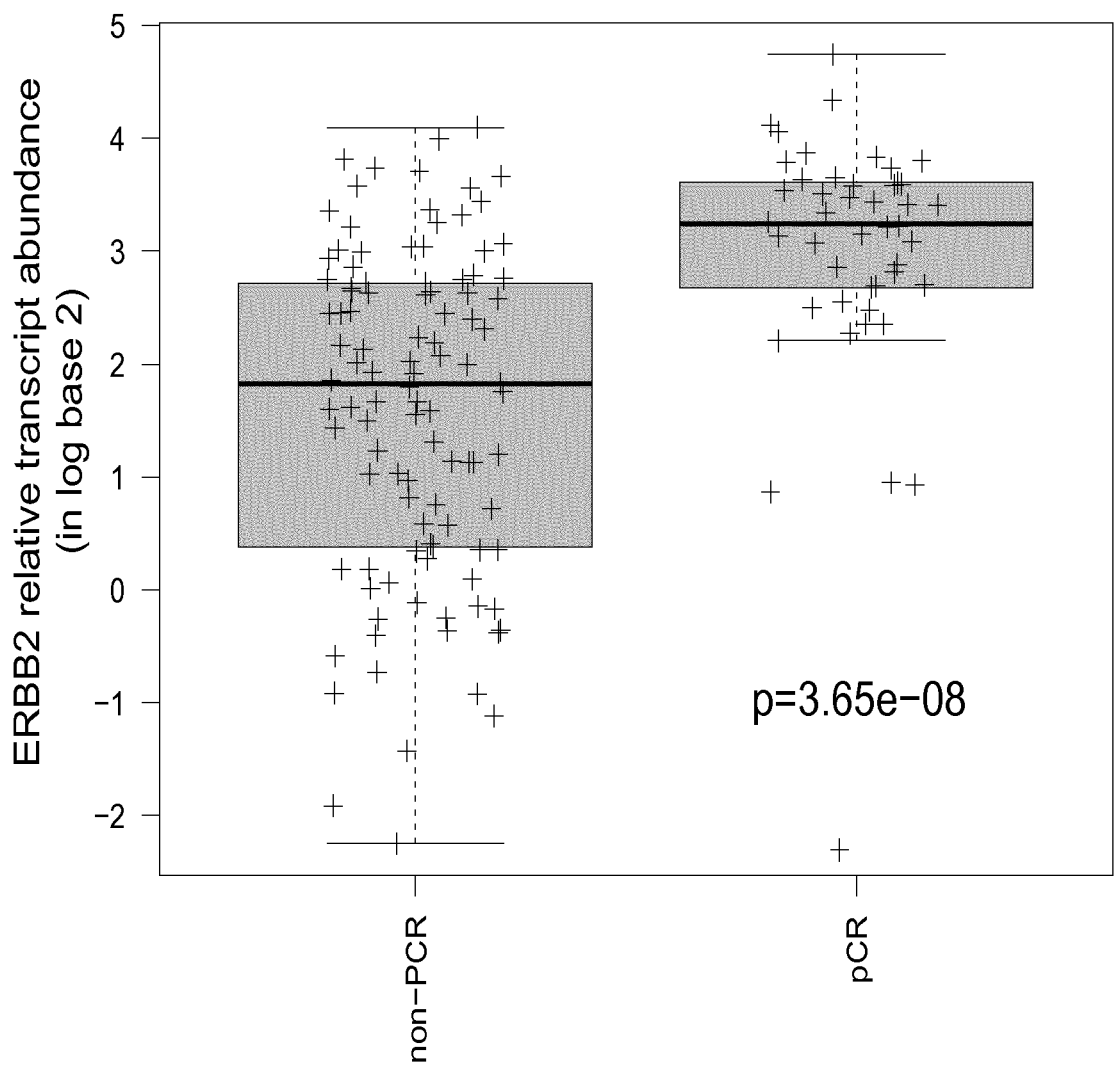

Prediction of pCR with ERBB2 Expression from Baseline Samples:

Overall, this data suggested that among the 555 breast cancer-related genes, ERBB2 was the most robust gene to predict response following dual HER2 blockade without chemotherapy. Then the ability of ERBB2 expression to predict pCR in the entire dataset of 151 patients with baseline tumour samples was explored. Firstly, it was estimated the performance of ERBB2 for predicting pCR (FIG. 5). The results revealed an AUC of 0.804.

Secondly, it was evaluated the expression of ERBB2 in patients that achieved a pCR versus those that did not (non-pCR) (FIG. 5). The results revealed that the median expression of ERBB2 in the pCR group was 3.24, and the median expression of ERBB2 in the non-pCR group was 1.83. The difference was 1.42, which is equivalent to a 2.68-fold difference. Thirdly, were explored the pCR rates according to ERBB2 expression. Using tertiles (cutoffs of ERBB2 score of 2.93 and 1.61), the pCR rate in the highest, intermediate and lowest tertiles were 58.8%, 24% and 8%, respectively. Using quartiles (cutoffs of ERBB2 score of 3.21, 2.45 and 0.97), the pCR rate in the highest, intermediate (the 2 intermediate quartiles combined into 1 group) and lowest quartiles were 64.9%, 23.7% and 10.5%, respectively.

Ability of ERBB2 at Baseline to Predict pCR Compared to HR Status:

HR status was the only molecular predictor to date to predict pCR following dual HER2 blockade in the absence of cytotoxic therapy. Here the ability of ERBB2 to predict pCR beyond HR status was evaluated. In a bivariate logistic regression model that includes HR status and ERBB2 expression (Table 4), it was observed that ERBB2 remains significantly associated with pCR whereas HR status loses its statistical significance. This results suggest that ERBB2 provides more predictive information than HR status.

TABLE 4

Association of ERBB2 baseline and HR with pCR.

| Signatures | N | Breast pCR rate | Univariate | | | | Bivariate | | | |
|---|---|---|---|---|---|---|---|---|---|---|
| | | | OR | Lower 95% | Upper 95% | p-value | OR | Lower 95% | Upper 95% | p-value |
| ERBB2 baseline HR status | 151 | NA | 2.62 | 1.8 | 3.9 | <0.001 | 2.41 | 1.6 | 3.7 | <0.001 |
| HR+ | 77 | 18.2% | 1 | — | — | — | 1 | — | — | — |
| HR-negative | 74 | 43.2% | 3.42 | 1.6 | 7.2 | 0.001 | 1.68 | 0.7 | 3.9 | 0.224 |

Figure 6:
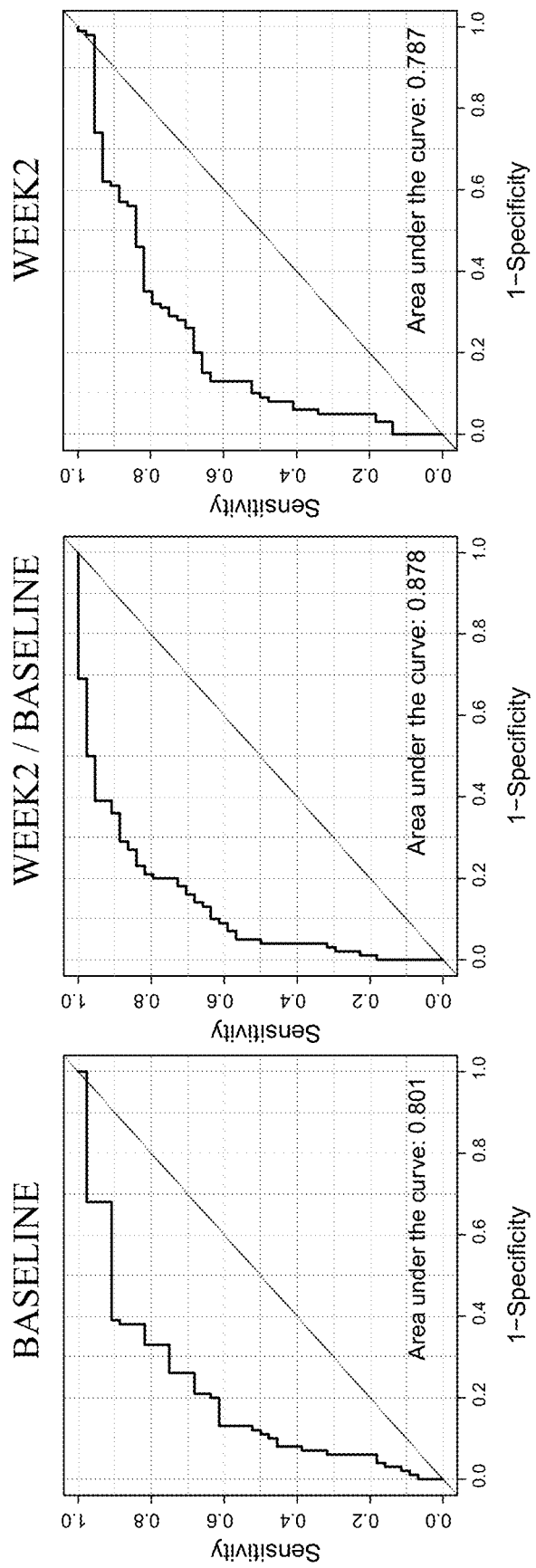
FIG. 6 shows the AUC analysis of ERBB2 expression (measured at baseline, ratio week 2/baseline or week 2) for predicting pCR in the entire dataset of paired samples (n=144).

Prediction of pCR with ERBB2 Expression at Baseline, Week 2 and Ratio Between Week 2 and Baseline:

A total of 144 paired samples were available in PAMELA from the 151 patients recruited. This represents 95% of all available samples. Thus, this paired dataset allowed to compare the predictive ability of ERBB2 expression measured at baseline, at week 2 and the ratio of ERBB2 expression between the 2 time-points. To compare performances, the AUCs between the three biomarkers were compared (FIG. 6). The results revealed that the ratio of ERBB2 expression between week 2 and baseline time-points was the best predictor of pCR (FIG. 6) with an AUC of 0.878.

Secondly, the pCR rates according to the ratio of ERBB2 expression between week 2 and baseline time-points were explored. Using tertiles (cutoffs of ERBB2 ratio score of −3.04 and −0.35), the pCR rate in the lowest, intermediate and highest tertiles were 64.6%, 25% and 2%, respectively. Using quartiles (cutoffs of ERBB2 ratio score of −3.88, −1.37 and 0.009), the pCR rate in the lowest, intermediate (the 2 intermediate quartiles combined into 1 group) and highest quartiles were 75%, 22.2% and 2.7%, respectively.

Figure 7:
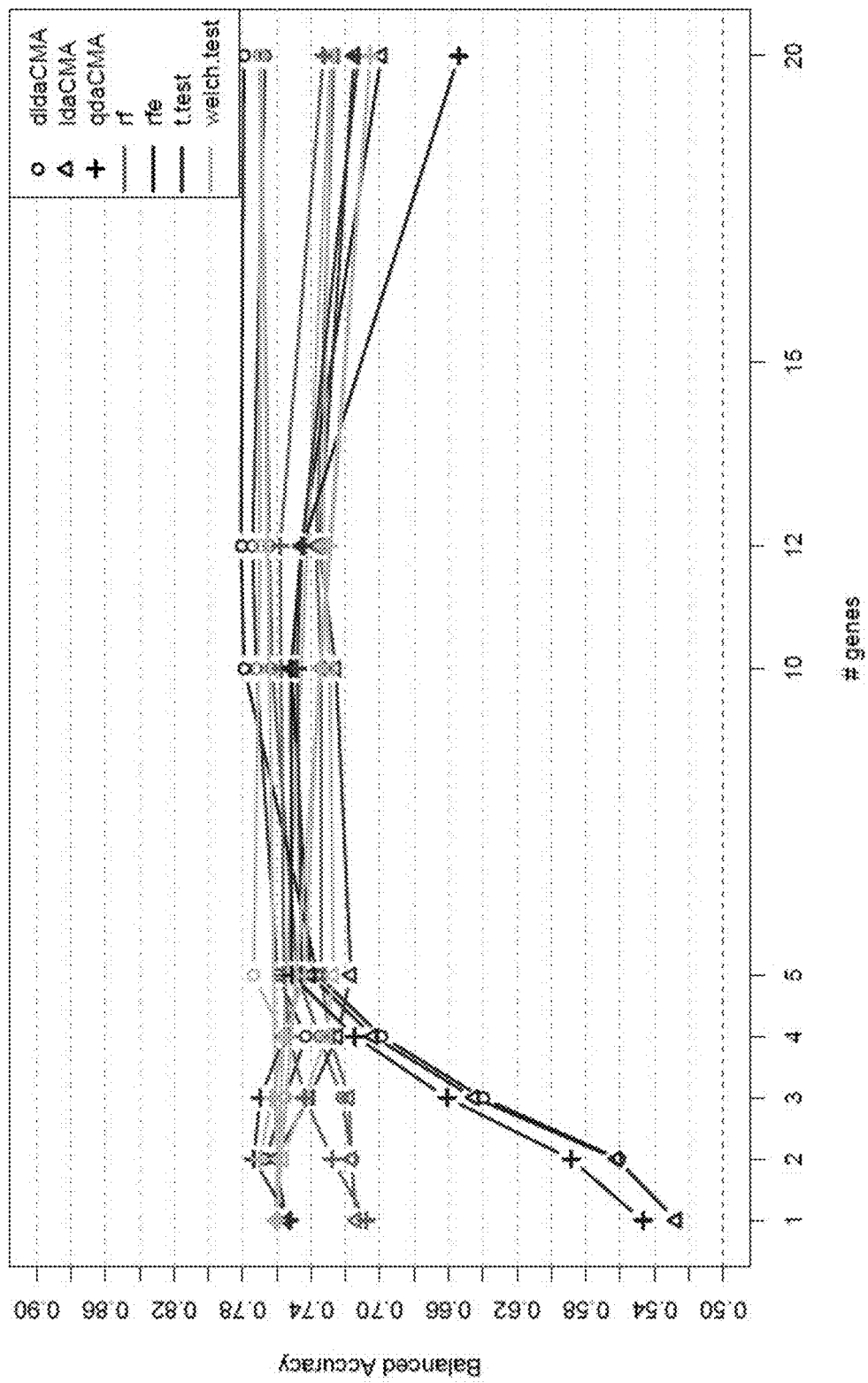
FIG. 7 Balanced accuracy analyses in using variable number of genes (ratio of week 2/baseline) and different methods of classification and variable selection. dlda, diagonal linear discriminant analysis; lda, linear discriminant analysis; qda, quadratic discriminant analysis; rf, random forests; rfe, recursive feature elimination; t.test, Student's t-test; welch.test, Welch's t-test.

Overall, this data suggested that the best predictor of pCR was the ratio of ERBB2 expression between week 2 and baseline time-points. However, it was unclear if this can be improved by the addition of genes. Thus, using the 555 breast cancer-related genes, we evaluated the best ratio of gene expression to predict pCR. To do so, was calculated the ratio of expression between week 2 and baseline time-points (i.e. week 2/baseline) for each gene. Similar to the previous analysis with baseline samples-only, we performed cross validation analyses (10-fold, repeated 25 times) using 4 methods of variable selection (t-test, Welch's t-test, random forests [rf] and recursive feature elimination [rfe]), different number of selected genes (1, 2, 3, 4, 5, 10, 12, 15, 20 and 30) and 3 classification methods (diagonal linear discriminant analysis [dlda], linear discriminant analysis [lda] and quadratic discriminant analysis [qda]). As shown in FIG. 7 and Table 5, similar 'balanced accuracies' were obtained with different number of genes. Of note, when using different methods of classification and variable selection, ERBB2 was found the top gene associated with pCR. These results suggested that not much prediction performance is to be gained by the addition of new genes beyond ERBB2.

TABLE 5

Genes selected during 10-fold cross-validation using different methods of classification and gene selection.

| Class. method | Variable Sel. Method | N. genes Sel. | Gene | M. | sensitivity | specificity | B. acc. |
|---|---|---|---|---|---|---|---|
| DLDA20 | rfe | 12 | — | 19.09% | 70.86% | 85.32% | 78.09% |
| DLDA21 | rfe | 20 | — | 19.74% | 71.98% | 83.88% | 77.93% |
| DLDA19 | rfe | 10 | — | 19.11% | 70.22% | 85.60% | 77.91% |
| DLDA6 | t.test | 12 | — | 21.20% | 74.00% | 80.84% | 77.42% |
| DLDA11 | welch.test | 5 | — | 20.85% | 72.70% | 82.00% | 77.35% |
| QDA2 | t.test | 2 | — | 17.55% | 64.30% | 90.40% | 77.35% |
| DLDA5 | t.test | 10 | — | 21.17% | 73.06% | 81.36% | 77.21% |

Figure 8:
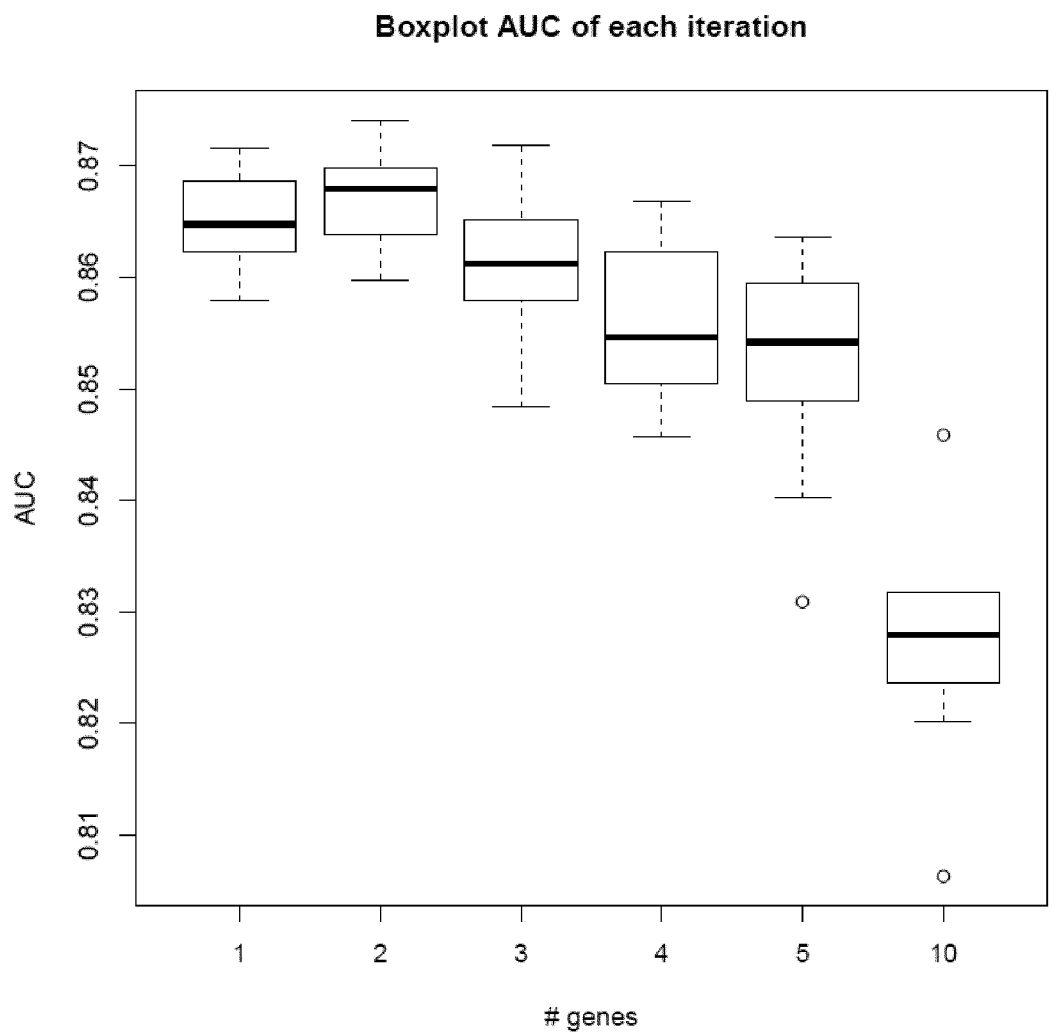
FIG. 8 shows the AUC analyses using week 2/baseline ratio after selection of 1, 2, 3, 4, 5 and 10 genes.

"Class. Method": Classification method;
"Variable Sel. Method": Variable Selection Method;
"N. genes Sel.": Number of genes selected;
"M.": misclassification;
"B. acc.": Balanced accuracy Furthermore, it was evaluated, using cross-validation analyses (10-fold, repeated 25 times) and the qda method, the prediction performance using Receiver Operating Characteristic (ROC) analysis (i.e. area under the ROC [auROC] curve) when 1, 2, 3, 4, 5 and 10 genes were selected. As shown in FIG. 8, 1 single gene, which was ERBB2 in all cases, showed one of the highest AUC. Indeed, a 2-gene model, which included ERBB2 and GRB7 (i.e. k=2), although they showed a numerically higher AUC, did not significantly improve the AUC compared to ERBB2-alone. Overall, this data suggested that among the 555 breast cancer-related genes, the ratio of ERBB2 expression between week 2 and baseline time-points was the most robust to predict response following dual HER2 blockade without chemotherapy.

Ability of ERBB2 Ratio to Predict pCR Compared to HR Status:

HR status was the only molecular predictor to date to predict pCR following dual HER2 blockade in the absence of cytotoxic therapy. Here the ability of ERBB2 ratio to predict pCR beyond HR status was evaluated. In a bivariate logistic regression model that includes HR status and ERBB2 ratio (Table 6), it was observed that ERBB2 ratio remains significantly associated with pCR whereas HR status loses its statistical significance. This results suggested that ERBB2 ratio provides more predictive information than HR status.

TABLE 6

Association of ERBB2 ratio and HR with pCR.

| Signatures | N | Breast pCR rate | OR | Univariate Lower 95% | Univariate Upper 95% | p-value | OR | Bivariate Lower 95% | Bivariate Upper 95% | p-value |
|---|---|---|---|---|---|---|---|---|---|---|
| ERBB2 ratio | 151 | NA | 0.49 | 0.4 | 0.6 | <0.001 | 0.51 | 0.4 | 0.6 | <0.001 |
| HR status | | | | | | | | | | |
| HR+ | 77 | 18.2% | 1 | — | — | — | 1 | — | — | — |
| HR-negative | 74 | 43.2% | 3.42 | 1.6 | 7.2 | 0.001 | 1.76 | 0.7 | 4.6 | 0.244 |

Ability of ERBB2 Ratio to Predict pCR Compared to ERBB2 Baseline

Here it was compared the ability of ERBB2 ratio to predict pCR compared to ERBB2 baseline in the 144 paired samples. In a bivariate logistic regression model that includes ERBB2 baseline and ratio (Table 7), it was observed that ERBB2 ratio remains significantly associated with pCR whereas ERBB2 baseline loses its statistical significance. This results suggest that ERBB2 ratio provides more predictive information than ERBB2 baseline, which is concordant with the previous AUC results.

TABLE 7

Association of ERBB2 ratio and ERBB2 baseline with pCR.

| Signatures | N | Breast pCR rate | OR | Univariate Lower 95% | Univariate Upper 95% | p-value | OR | Bivariate Lower 95% | Bivariate Upper 95% | p-value |
|---|---|---|---|---|---|---|---|---|---|---|
| ERBB2 baseline | 151 | NA | 2.56 | 1.7 | 3.8 | <0.001 | 1.39 | 0.9 | 2.2 | 0.149 |
| ERBB2 ratio | 151 | NA | 0.49 | 0.4 | 0.6 | <0.001 | 0.54 | 0.4 | 0.7 | <0001 |

CONCLUSIONS

In this study, it has been shown that ERBB2 expression alone is the best predictor of pCR following dual HER2 blockade without chemotherapy. This biomarker can be evaluated either at baseline, at week 2 of treatment, or both. These results suggest that the predictive ability of baseline ERBB2 expression is similar to week 2 ERBB2 expression; however, combination of ERBB2 expression data coming from both time-points (i.e. ERBB2 ratio) is the best predictor among the three. Thus, from a clinical perspective, ERBB2 expression could be used either at baseline-only (i.e. before starting therapy) or at both time-points (i.e. ERBB2 ratio) if a biopsy at week 2 is available. Either way, both predictors can identify ~25% (top quartile) of patients with HER2+ disease that will achieve a pCR in 64.9-75% of the cases if treated with dual HER2 blockade without chemotherapy. Importantly, ERBB2 at baseline, or ERBB2 ratio, provide independent and more information compared to HR status, which is the only molecular predictor to date consistently found associated with pCR in HER2+ breast cancer following dual HER2 blockade without chemotherapy.

REFERENCES

1. Wolff A C, Hammond M E H, Hicks D G, et al. Recommendations for Human Epidermal Growth Factor Receptor 2 Testing in Breast Cancer: American Society of Clinical Oncology/College of American Pathologists Clinical Practice Guideline Update. *Journal of Clinical Oncology* 2013; 31(31): 3997-4013.
2. Slamon D, Eiermann W, Robert N, et al. Adjuvant Trastuzumab in HER2-Positive Breast Cancer. *New England Journal of Medicine* 2011; 365(14): 1273-83.
3. Blackwell K L, Burstein H J, Storniolo A M, et al. Overall Survival Benefit With Lapatinib in Combination With Trastuzumab for Patients With Human Epidermal Growth Factor Receptor 2-Positive Metastatic Breast Cancer: Final Results From the EGF104900 Study. *Journal of Clinical Oncology* 2012; 30(21): 2585-92.
4. Baselga J, Cortés J, Kim S-B, et al. Pertuzumab plus Trastuzumab plus Docetaxel for Metastatic Breast Cancer. *New England Journal of Medicine* 2012; 366(2): 109-19.
5. Cortazar P, Zhang L, Untch M, et al. Pathological complete response and long-term clinical benefit in breast cancer: the CTNeoBC pooled analysis. *The Lancet;* 384 (9938): 164-72.
6. Piccart-Gebhart M, Holmes E, Baselga J, et al. Adjuvant Lapatinib and Trastuzumab for Early Human Epidermal Growth Factor Receptor 2—Positive Breast Cancer: Results From the Randomized Phase III Adjuvant Lapatinib and/or Trastuzumab Treatment Optimization Trial. *Journal of Clinical Oncology* 2016; 34(10): 1034-42.
7. Tolaney S M, Barry W T, Dang C T, et al. Adjuvant Paclitaxel and Trastuzumab for Node-Negative, HER2-Positive Breast Cancer. *New England Journal of Medicine* 2015; 372(2): 134-41.
8. Fumagalli D, Venet D, Ignatiadis M, et al. Rna sequencing to predict response to neoadjuvant anti-her2 therapy: A secondary analysis of the neoaltto randomized clinical trial. *JAMA Oncology* 2016.
9. Carey L A, Berry D A, Cirrincione C T, et al. Molecular Heterogeneity and Response to Neoadjuvant Human Epidermal Growth Factor Receptor 2 Targeting in CALGB 40601, a Randomized Phase III Trial of Paclitaxel Plus Trastuzumab With or Without Lapatinib. *Journal of Clinical Oncology* 2015.
10. Schneeweiss A, Chia S, Hickish T, et al. Pertuzumab plus trastuzumab in combination with standard neoadjuvant anthracycline-containing and anthracycline-free chemotherapy regimens in patients with HER2-positive early breast cancer: a randomized phase II cardiac safety study (TRYPHAENA). *Annals of Oncology* 2013; 24(9): 2278-84.

11. Baselga J, Bradbury I, Eidtmann H, et al. Lapatinib with trastuzumab for HER2-positive early breast cancer (NeoALTTO): a randomised, open-label, multicentre, phase 3 trial. *The Lancet* 2012; 379(9816): 633-40.

12. Scaltriti M, Nuciforo P, Bradbury I, et al. High HER2 Expression Correlates with Response to the Combination of Lapatinib and Trastuzumab. *Clinical Cancer Research* 2015; 21(3): 569-76.

13. Hayes D F, Thor A D, Dressler L G, et al. HER2 and Response to Paclitaxel in Node-Positive Breast Cancer. *New England Journal of Medicine* 2007; 357(15): 1496-506.

14. Gianni L, Pienkowski T, Im Y-H, et al. Efficacy and safety of neoadjuvant pertuzumab and trastuzumab in women with locally advanced, inflammatory, or early HER2-positive breast cancer (NeoSphere): a randomised multicentre, open-label, phase 2 trial. *The Lancet Oncology* 2012; 13(1): 25-32.

15. Rimawi M F, Mayer I A, Forero A, et al. Multicenter Phase II Study of Neoadjuvant Lapatinib and Trastuzumab With Hormonal Therapy and Without Chemotherapy in Patients With Human Epidermal Growth Factor Receptor 2—Overexpressing Breast Cancer: TBCRC 006. *Journal of Clinical Oncology* 2013; 31(14): 1726-31.

16. Cortés J, Fumoleau P, Bianchi G V, et al. Pertuzumab Monotherapy After Trastuzumab-Based Treatment and Subsequent Reintroduction of Trastuzumab: Activity and Tolerability in Patients With Advanced Human Epidermal Growth Factor Receptor 2—Positive Breast Cancer. *Journal of Clinical Oncology* 2012; 30(14): 1594-600.

TABLE 8 nCounter™ CodeSet Design for the 560 genes

| Gene | Accession | T.Region | Gene | Accession | T.Region |
|---|---|---|---|---|---|
| A1CF | NM_014576.2 | 1866-1965 | BAG1 | NM_004323.3 | 1491-1590 |
| AARS | NM_001605.2 | 836-935 | BCL11A | NM_018014.2 | 3781-3880 |
| ABAT | NM_000663.4 | 3336-3435 | BCL2 | NM_000633.2 | 1526-1625 |
| ABCB1 | NM_000927.3 | 3911-4010 | BCL2A1 | NM_001114735.1 | 1-100 |
| ABCC3 | NM_001144070.1 | 461-560 | BDNF | NM_001143805.1 | 436-535 |
| ABCC8 | NM_000352.3 | 481-580 | BIRC5 | NM_001012270.1 | 1096-1195 |
| ACOT4 | NM_152331.3 | 733-832 | BLM | NM_000057.2 | 2136-2235 |
| ACTB | NM_001101.2 | 1011-1110 | BLVRA | NM_000712.3 | 926-1025 |
| ACTL8 | NM_030812.1 | 1611-1710 | BMI1 | NM_005180.5 | 1146-1245 |
| ACTR3B | NM_001040135.1 | 276-375 | BOP1 | NM_015201.3 | 204-303 |
| ADM | NM_001124.1 | 1301-1400 | BRAF | NM_004333.3 | 566-665 |
| ADRA2A | NM_000681.2 | 2491-2590 | BRCA1 | NM_007294.2 | 631-730 |
| ADRA2C | NM_000683.3 | 1366-1465 | BRCA2 | NM_000059.3 | 116-215 |
| AFF3 | NM_001025108.1 | 4881-4980 | BTG2 | NM_006763.2 | 1701-1800 |
| AGR2 | NM_006408.2 | 1366-1465 | BTG3 | NM_001130914.1 | 876-975 |
| AGR3 | NM_176813.3 | 1-100 | BUB1 | NM_004336.2 | 101-200 |
| AHCYL1 | NM_006621.4 | 2436-2535 | BYSL | NM_004053.3 | 1081-1180 |
| AKT1 | NM_001014431.1 | 2008-2107 | C11orf30 | NM_020193.3 | 2226-2325 |
| AKT3 | NM_005465.3 | 2001-2100 | C16orf45 | NM_001142469.1 | 1621-1720 |
| ALDH1A1 | NM_000689.3 | 12-111 | C1orf106 | NM_001142569.1 | 2561-2660 |
| ANGPTL4 | NM_001039667.1 | 1137-1236 | C1orf21 | NM_030806.3 | 8911-9010 |
| ANLN | NM_018685.2 | 1901-2000 | C4orf32 | NM_152400.1 | 181-280 |
| ANXA1 | NM_000700.1 | 516-615 | C8orf33 | NM_023080.2 | 1366-1465 |
| ANXA8L2 | NM_001630.2 | 1351-14500 | CA12 | NM_001218.3 | 2446-2545 |
| APC | NM_000038.3 | 6851-6950 | CABP7 | NM_182527.2 | 2741-2840 |
| APH1B | NM_001145646.1 | 2931-3030 | CAMK2N1 | NM_018584.5 | 86-185 |
| AR | NM_000044.2 | 876-975 | CAND1 | NM_018448.3 | 2821-2920 |
| ARAF | NM_001654.1 | 1021-1120 | CAPN13 | NM_144575.2 | 1266-1365 |
| AREG | NM_001657.2 | 548-647 | CAPN6 | NM_014289.2 | 1131-1230 |
| ASF1A | NM_014034.2 | 351-450 | CAV1 | NM_001753.3 | 435-534 |
| C12orf11 | NM_018164.2 | 906-1005 | CBX7 | NM_175709.3 | 2556-2655 |
| ATAD2 | NM_014109.3 | 1036-113500 | CCDC86 | NM_024098.3 | 1461-1560 |
| ATAD3A | NM_001170535.1 | 501-600 | CCNA2 | NM_001237.2 | 1211-1310 |
| ATM | NM_000051.3 | 31-130 | CCNB1 | NM_031966.2 | 716-815 |
| ATR | NM_001184.2 | 566-665 | CCND1 | NM_053056.2 | 691-790 |
| AURKA | NM_003600.2 | 406-505 | CCND2 | NM_001759.2 | 5826-5925 |
| AVEN | NM_020371.2 | 441-540 | CCND3 | NM_001136017.2 | 1934-2033 |
| AVL9 | NM_015060.1 | 1346-1445 | CCNE1 | NM_001238.1 | 1636-1735 |
| AXL | NM_001699.4 | 1898-1997 | CD19 | NM_001178098.1 | 939-1038 |
| AZGP1 | NM_001185.2 | 124-223 | CD24 | NM_013230.2 | 96-195 |
| CD3G | NM_000073.2 | 405-504 | CHEK1 | NM_001114121.1 | 2226-2325 |
| CD4 | NM_000616.3 | 836-935 | CHEK2 | NM_001005735.1 | 536-635 |
| CD44 | NM_000610.3 | 2461-2560 | CHPF | NM_024536.5 | 2905-3004 |
| CD68 | NM_001040059.1 | 1571-1670 | CHST11 | NM_018413.4 | 326-425 |
| CD84 | NM_001184882.1 | 76-175 | CHUK | NM_001278.3 | 861-960 |
| CD86 | NM_006889.3 | 147-246 | CITED4 | NM_133467.2 | 916-1015 |
| CD8A | NM_001768.5 | 1321-1420 | CKS1B | NM_001826.2 | 239-338 |
| CDA | NM_001785.2 | 323-422 | CKS2 | NM_001827.1 | 196-295 |
| CDC123 | NM_006023.1 | 496-595 | CLDN3 | NM_001306.3 | 607-706 |
| CDC20 | NM_001255.2 | 431-530 | CLDN4 | NM_001305.3 | 1243-1342 |
| CDC25B | NM_004358.3 | 3006-3105 | CLDN7 | NM_001307.3 | 176-275 |
| CDC25C | NM_001790.2 | 1056-1155 | CLMN | NM_024734.3 | 3336-3435 |

TABLE 8-continued nCounter™ CodeSet Design for the 560 genes

| Gene | Accession | T.Region | Gene | Accession | T.Region |
|---|---|---|---|---|---|
| CDC45L | NM_003504.3 | 1676-1775 | C16orf61 | NM_020188.3 | 532-631 |
| CDC6 | NM_001254.3 | 1301-1400 | COG8 | NM_032382.4 | 1151-1250 |
| CDCA5 | NM_080668.3 | 321-420 | COX6C | NM_004374.2 | 70-169 |
| CDCA7 | NM_031942.4 | 771-870 | COX7B | NM_001866.2 | 4-103 |
| CDCA7L | NM_001127370.1 | 71-170 | CRIM1 | NM_016441.1 | 1521-1620 |
| CDCA8 | NM_018101.2 | 1666-1765 | CRYAB | NM_001885.1 | 579-678 |
| CDH1 | NM_004360.2 | 1231-1330 | CTGF | NM_001901.2 | 1101-1200 |
| CDH3 | NM_001793.4 | 3746-3845 | CTNNB1 | NM_001098209.1 | 1811-1910 |
| CDK1 | NM_001170406.1 | 700-799 | CTPS | NM_001905.2 | 2571-2670 |
| CDK4 | NM_000075.2 | 1056-1155 | CTSL1 | NM_001912.4 | 1073-1172 |
| CDKN1A | NM_000389.2 | 1976-2075 | CTSL2 | NM_001333.2 | 66-165 |
| CDKN1B | NM_004064.2 | 366-465 | CXCL1 | NM_001511.1 | 446-545 |
| CDKN2A | NM_000077.3 | 976-1075 | CXCL14 | NM_004887.4 | 1126-1225 |
| CDKN2B | NM_004936.3 | 1176-1275 | IL8 | NM_000584.2 | 26-125 |
| CDKN2C | NM_001262.2 | 1296-1395 | CXCR1 | NM_000634.2 | 1951-2050 |
| CDKN2D | NM_001800.3 | 871-970 | CXCR2 | NM_001168298.1 | 113-212 |
| CDKN3 | NM_001130851.1 | 391-490 | CXXC5 | NM_016463.7 | 1266-1365 |
| CDT1 | NM_030928.3 | 1437-1536 | CYB5B | NM_030579.2 | 481-580 |
| CDYL | NM_001143970.1 | 1591-1690 | CYBRD1 | NM_001127383.1 | 1216-1315 |
| CEACAM6 | NM_002483.4 | 1218-1317 | CYCS | NM_018947.4 | 1736-1835 |
| CELSR1 | NM_014246.1 | 10056-10155 | CYR61 | NM_001554.3 | 1391-1490 |
| CENPA | NM_001042426.1 | 980-1079 | DDB2 | NM_000107.1 | 841-940 |
| CENPF | NM_016343.3 | 5823-5922 | DDIT4 | NM_019058.2 | 86-185 |
| CENPI | NM_006733.2 | 661-760 | DDR1 | NM_001954.4 | 1343-1442 |
| CENPN | NM_001100624.1 | 1941-2040 | DEGS2 | NM_206918.2 | 398-497 |
| CEP55 | NM_001127182.1 | 559-658 | DLGAP5 | NM_001146015.1 | 131-230 |
| CFLAR | NM_001127183.1 | 654-753 | DNAJC12 | NM_021800.2 | 621-720 |
| DNALI1 | NM_003462.3 | 1786-1885 | FLVCR2 | NM_017791.2 | 1256-1355 |
| DSP | NM_001008844.1 | 6026-6125 | FNBP1 | NM_015033.2 | 1341-1440 |
| E2F1 | NM_005225.1 | 936-1035 | FOXA1 | NM_004496.2 | 2466-2565 |
| ECE2 | NM_001037324.2 | 1096-1195 | FOXC1 | NM_001453.1 | 1516-1615 |
| EGFR | NM_005228.3 | 2761-2860 | FOXM1 | NM_021953.2 | 3209-3308 |
| EIF2S2 | NM_003908.3 | 1611-1710 | FZD6 | NM_001164615.1 | 1231-1330 |
| ELOVL5 | NM_021814.3 | 2081-2180 | FZD7 | NM_003507.1 | 1891-1990 |
| ELSPBP1 | NM_022142.3 | 151-250 | GABPB1 | NM_002041.4 | 726-825 |
| COX4NB | NM_001142288.1 | 861-960 | GAL | NM_015973.3 | 445-544 |
| EMP3 | NM_001425.2 | 351-450 | GALNT7 | NM_017423.2 | 911-1010 |
| EPCAM | NM_002354.1 | 416-515 | GARS | NM_002047.2 | 1231-1330 |
| EPN3 | NM_017957.2 | 2533-2632 | GATA3 | NM_001002295.1 | 2836-2935 |
| EPSTI1 | NM_001002264.1 | 611-710 | GGH | NM_003878.2 | 693-792 |
| ERBB2 | NM_001005862.1 | 1256-1355 | GINS2 | NM_016095.2 | 991-1090 |
| ERBB3 | NM_001005915.1 | 421-520 | GLRB | NM_000824.3 | 1236-1335 |
| ERBB4 | NM_001042599.1 | 7301-7400 | GNG11 | NM_004126.3 | 431-530 |
| ERCC1 | NM_001166049.1 | 2856-2955 | GOLT1A | NM_198447.1 | 266-365 |
| ESR1 | NM_000125.2 | 2391-2490 | GPR160 | NM_014373.1 | 761-860 |
| ESRP1 | NM_001034915.2 | 1516-1615 | GPR89A | NM_001097612.1 | 1482-1581 |
| EVI2A | NM_001003927.1 | 246-345 | GPSM2 | NM_013296.3 | 1931-2030 |
| EXO1 | NM_003686.3 | 2716-2815 | GRB7 | NM_001030002.1 | 971-1070 |
| EZH2 | NM_004456.3 | 191-290 | GREM1 | NM_013372.5 | 576-675 |
| F11R | NM_016946.4 | 2106-2205 | GRHL1 | NM_198182.1 | 941-1040 |
| F3 | NM_001993.3 | 1031-1130 | GRHL2 | NM_024915.3 | 3691-3790 |
| FABP4 | NM_001442.2 | 416-515 | GSTM1 | NM_000561.2 | 336-435 |
| FABP5 | NM_001444.1 | 101-200 | GSTM3 | NM_000849.3 | 1026-1125 |
| FAM171A1 | NM_001010924.1 | 2936-3035 | GSTM4 | NM_000850.4 | 61-160 |
| FAM174B | NM_207446.2 | 1076-1175 | GSTP1 | NM_000852.2 | 416-515 |
| FAM198B | NM_001031700.2 | 1631-1730 | GTPBP4 | NM_012341.2 | 81-180 |
| KIAA1370 | NM_019600.2 | 3266-3365 | GUSB | NM_000181.1 | 1351-1450 |
| FANCA | NM_000135.2 | 266-365 | H19 | NR_002196.1 | 1593-1692 |
| FANK1 | NM_145235.3 | 446-545 | HEXIM1 | NM_006460.2 | 2921-3020 |
| FAP | NM_004460.2 | 1491-1590 | C8orf30A | NM_016458.2 | 2226-2325 |
| FBN1 | NM_000138.3 | 6421-6520 | HIF1A | NM_001530.2 | 1986-2085 |
| FBP1 | NM_000507.3 | 591-690 | HJURP | NM_018410.3 | 1326-1425 |
| FBXL6 | NM_012162.1 | 548-647 | HMGA1 | NM_002131.3 | 92-191 |
| FGFR1 | NM_015850.3 | 1336-1435 | HN1 | NM_001002032.1 | 711-810 |
| FGFR2 | NM_000141.4 | 706-805 | HRAS | NM_001130442.1 | 397-496 |
| FGFR4 | NM_002011.3 | 1586-1685 | HSPA14 | NM_016299.2 | 1331-1430 |
| FIGF | NM_004469.2 | 581-680 | HSPD1 | NM_002156.4 | 924-1023 |
| ID4 | NM_001546.2 | 2049-2148 | KRT14 | NM_000526.4 | 524-623 |
| IDH2 | NM_002168.2 | 426-525 | KRT16 | NM_005557.3 | 1391-1490 |
| IDO1 | NM_002164.3 | 51-150 | KRT17 | NM_000422.2 | 515-614 |
| IFT74 | NM_001099222.1 | 136-235 | KRT18 | NM_000224.2 | 841-940 |
| IGBP1 | NM_001551.1 | 1486-1585 | KRT19 | NM_002276.4 | 97-196 |
| IGF1 | NM_000618.3 | 492-591 | KRT23 | NM_015515.3 | 1736-1835 |
| IGF2R | NM_000876.1 | 2606-2705 | KRT5 | NM_000424.2 | 131-230 |
| IGFBP2 | NM_000597.2 | 676-775 | KRT6A | NM_005554.3 | 118-217 |
| IKBKB | NM_001556.1 | 1996-2095 | KRT6B | NM_005555.3 | 2096-2195 |

TABLE 8-continued nCounter™ CodeSet Design for the 560 genes

| Gene | Accession | T.Region | Gene | Accession | T.Region |
|---|---|---|---|---|---|
| IKBKE | NM_014002.2 | 2471-2570 | KRT6C | NM_173086.4 | 1854-1953 |
| IL1B | NM_000576.2 | 841-940 | KRT8 | NM_002273.3 | 360-459 |
| IL6 | NM_000600.1 | 221-320 | KRTAP1-1 | NM_030967.2 | 565-664 |
| IL6R | NM_000565.2 | 994-1093 | LAG3 | NM_002286.5 | 1736-1835 |
| IL6ST | NM_002184.2 | 2506-2605 | LAMA3 | NM_000227.3 | 4261-4360 |
| INHBA | NM_002192.2 | 491-590 | LAMC2 | NM_005562.2 | 4296-4395 |
| INPP4B | NM_001101669.1 | 3056-3155 | LEPRE1 | NM_001146289.1 | 861-960 |
| INSIG1 | NM_005542.3 | 1121-1220 | LHFP | NM_005780.2 | 461-560 |
| IRX3 | NM_024336.1 | 2103-2202 | h.LOC389332 | NR_024418.1 | 1606-1705 |
| ITCH | NM_031483.4 | 156-255 | h.LOC400043 | NR_026656.1 | 1056-1155 |
| ITGA6 | NM_000210.1 | 3066-3165 | h.LOC642077 | XM_942735.1 | 262-361 |
| ITGB1 | NM_002211.3 | 356-455 | h.LOC647456 | XM_942813.1 | 121-220 |
| JUP | NM_002230.2 | 1076-1175 | s.Cytokeratin-8 | XM_937689.1 | 813-912 |
| KCNJ15 | NM_002243.3 | 2161-2260 | LRIG1 | NM_015541.2 | 571-670 |
| KCTD1 | NM_001136205.1 | 1368-1467 | LRP8 | NM_001018054.1 | 2091-2190 |
| KDM4B | NM_015015.2 | 121-220 | LRRC2 | NM_024512.3 | 111-210 |
| KDR | NM_002253.2 | 1421-1520 | LSR | NM_015925.5 | 804-903 |
| KIAA0040 | NM_001162893.1 | 2791-2890 | LTBP2 | NM_000428.2 | 5985-6084 |
| KIAA1324 | NM_020775.2 | 1806-1905 | MAD2L1 | NM_002358.3 | 183-282 |
| KIF13B | NM_015254.3 | 116-215 | MAGEA1 | NM_004988.4 | 477-576 |
| KIF20A | NM_005733.2 | 301-400 | MAGOHB | NM_018048.2 | 1523-1622 |
| KIF23 | NM_004856.4 | 2721-2820 | MAP2K1 | NM_002755.2 | 971-1070 |
| KIF2C | NM_006845.3 | 1941-2040 | MAP2K4 | NM_003010.2 | 2831-2930 |
| KIF4A | NM_012310.3 | 3232-3331 | MAP7D3 | NM_024597.2 | 806-905 |
| KIFC1 | NM_002263.3 | 1547-1646 | MAPT | NM_001123066.2 | 5606-5705 |
| KIT | NM_000222.1 | 6-105 | MCM2 | NM_004526.2 | 2946-3045 |
| KLF4 | NM_004235.4 | 1981-2080 | MCM3 | NM_002388.3 | 301-400 |
| KLHL7 | NM_001031710.2 | 1681-1780 | MDM2 | NM_001145337.1 | 5871-5970 |
| KLHL9 | NM_018847.1 | 3581-3680 | ME1 | NM_002395.3 | 1406-1505 |
| KPNA1 | NM_002264.2 | 1421-1520 | MED21 | NM_004264.3 | 124-223 |
| KRAS | NM_004985.3 | 1791-1890 | MELK | NM_014791.2 | 366-465 |
| MET | NM_000245.2 | 406-505 | NFKBIB | NM_001001716.1 | 1256-1355 |
| h.MGC18216 | XM_927732.1 | 2824-2923 | NFKBIE | NM_004556.2 | 1116-1215 |
| MIA | NM_006533.2 | 117-216 | NLN | NM_020726.2 | 961-1060 |
| C17orf37 | NM_032339.3 | 291-390 | NOP56 | NM_006392.2 | 606-705 |
| C21orf45 | NM_018944.2 | 681-780 | NOTCH1 | NM_017617.3 | 736-835 |
| MK167 | NM_001145966.1 | 9171-9270 | NOTCH2 | NM_024408.2 | 5086-5185 |
| MKRN2 | NM_014160.3 | 2251-2350 | NOTCH3 | NM_000435.2 | 1966-2065 |
| MLKL | NM_001142497.1 | 716-815 | NPEPPS | NM_006310.3 | 3381-3480 |
| MLPH | NM_001042467.1 | 3156-3255 | NPM2 | NM_182795.1 | 746-845 |
| MME | NM_000902.2 | 5060-5159 | NQO1 | NM_000903.2 | 791-890 |
| MMP11 | NM_005940.3 | 261-360 | NR4A3 | NM_006981.2 | 1841-1940 |
| MPP1 | NM_001166460.1 | 1596-1695 | NRAS | NM_002524.3 | 878-977 |
| MRPL19 | NM_014763.3 | 365-464 | NT5E | NM_002526.2 | 1215-1314 |
| MRPS17 | NM_015969.2 | 181-280 | NTN4 | NM_021229.3 | 2121-2220 |
| MRPS35 | NM_021821.2 | 251-350 | NUDCD1 | NM_001128211.1 | 81-180 |
| MS4A1 | NM_152866.2 | 621-720 | NUDT1 | NM_002452.3 | 394-493 |
| MSH2 | NM_000251.1 | 2106-2205 | NUF2 | NM_031423.3 | 931-1030 |
| FAM54A | NM_001099286.1 | 1046-1145 | NUP88 | NM_002532.3 | 1411-1510 |
| MTHFD1L | NM_015440.3 | 1101-1200 | NUP93 | NM_014669.3 | 646-745 |
| MTOR | NM_004958.2 | 5096-5195 | OCLN | NM_002538.2 | 596-695 |
| MUC1 | NM_001018016.1 | 436-535 | OGFRL1 | NM_024576.3 | 1036-1135 |
| MUC5B | NM_002458.1 | 16312-16411 | OGN | NM_014057.3 | 996-1095 |
| MYB | NM_001130172.1 | 3121-3220 | ORC6L | NM_014321.2 | 583-682 |
| MYBL2 | NM_002466.2 | 446-545 | P4HTM | NM_177938.2 | 1616-1715 |
| MYC | NM_002467.3 | 1611-1710 | PARP1 | NM_001618.3 | 3017-3116 |
| MYO5C | NM_018728.2 | 2401-2500 | PCDH8 | NM_002590.2 | 3386-3485 |
| NACC2 | NM_144653.3 | 1936-2035 | PCNA | NM_002592.2 | 281-380 |
| NAT1 | NM_000662.4 | 1-100 | PDCD1 | NM_005018.1 | 176-275 |
| NCAPH2 | NM_014551.4 | 304-403 | PDGFRA | NM_006206.3 | 1926-2025 |
| FREQ | NM_001128826.1 | 2896-2995 | PDSS1 | NM_014317.3 | 531-630 |
| NDC80 | NM_006101.2 | 97-196 | PDXK | NM_003681.3 | 581-680 |
| NDRG1 | NM_001135242.1 | 2721-2820 | PEX11G | NM_080662.2 | 205-304 |
| NDUFAF4 | NM_014165.2 | 1057-1156 | PGAM5 | NM_001170543.1 | 968-1067 |
| NEK2 | NM_002497.2 | 1346-1445 | PGR | NM_000926.4 | 2721-2820 |
| NEO1 | NM_002499.2 | 2431-2530 | PHGDH | NM_006623.3 | 1901-2000 |
| NF1 | NM_000267.2 | 1036-1135 | PID1 | NM_001100818.1 | 311-410 |
| NFIA | NM_001134673.2 | 1086-1185 | FAM38A | NM_001142864.1 | 446-545 |
| NFIB | NM_005596.2 | 3831-3930 | PIK3CA | NM_006218.2 | 2446-2545 |
| NFKB1 | NM_001165412.1 | 2306-2405 | PIK3R1 | NM_181504.2 | 1106-1205 |
| NFKBIA | NM_020529.1 | 946-1045 | PIP | NM_002652.2 | 301-400 |
| PIR | NM_001018109.1 | 746-845 | RBBP8 | NM_002894.2 | 761-860 |
| PITX1 | NM_002653.4 | 1551-1650 | RECK | NM_021111.2 | 2136-2235 |
| PLA1A | NM_015900.2 | 1251-1350 | RECQL | NM_002907.3 | 1251-1350 |
| PLOD1 | NM_000302.2 | 966-1065 | REEP6 | NM_138393.1 | 387-486 |
| PNO1 | NM_020143.2 | 716-815 | RELA | NM_001145138.1 | 2356-2455 |

TABLE 8-continued nCounter™ CodeSet Design for the 560 genes

| Gene | Accession | T.Region | Gene | Accession | T.Region |
|---|---|---|---|---|---|
| PNP | NM_000270.2 | 1151-1250 | RELB | NM_006509.2 | 251-350 |
| POLD1 | NM_002691.2 | 2393-2492 | RERG | NM_032918.1 | 526-625 |
| PPFIBP1 | NM_003622.2 | 2586-2685 | RFC4 | NM_002916.3 | 956-1055 |
| SAPS1 | NM_014931.3 | 781-880 | RGS22 | NM_015668.3 | 2576-2675 |
| PRAME | NM_006115.3 | 1391-1490 | RHBG | NM_020407.2 | 661-760 |
| PRC1 | NM_003981.2 | 2046-2145 | RINT1 | NM_021930.4 | 1806-1905 |
| PREP | NM_002726.3 | 1451-1550 | RNF103 | NM_005667.2 | 2891-2990 |
| PROM1 | NM_001145847.1 | 601-700 | RPLPO | NM_001002.3 | 251-350 |
| PSMA7 | NM_002792.2 | 640-739 | RRAGD | NM_021244.4 | 2281-2380 |
| PSMC4 | NM_006503.2 | 251-350 | RRM2 | NM_001034.1 | 1616-1715 |
| PSMD14 | NM_005805.4 | 701-800 | RRP15 | NM_016052.3 | 7076-7175 |
| PSPH | NM_004577.3 | 226-325 | S100A11 | NM_005620.1 | 474-573 |
| PSPHL | AJ001612.1 | 1-100 | S100A14 | NM_020672.1 | 461-560 |
| PTDSS1 | NM_014754.1 | 2376-2475 | S100A8 | NM_002964.3 | 116-215 |
| PTEN | NM_000314.3 | 1676-1775 | S100A9 | NM_002965.2 | 76-175 |
| PTGER4 | NM_000958.2 | 1381-1480 | SCGB2A2 | NM_002411.1 | 266-365 |
| PTGS2 | NM_000963.1 | 496-595 | SCUBE2 | NM_001170690.1 | 2291-2390 |
| PTTG1 | NM_004219.2 | 543-642 | SEH1L | NM_001013437.1 | 501-600 |
| PUF60 | NM_001136033.1 | 1686-1785 | SEMA3C | NM_006379.2 | 946-1045 |
| PUM1 | NM_001020658.1 | 641-740 | SERPINA3 | NM_001085.4 | 6-105 |
| PVRL3 | NM_015480.1 | 1111-1210 | SETBP1 | NM_001130110.1 | 1071-1170 |
| PYROXD1 | NM_024854.3 | 1049-1148 | SF3A1 | NM_001005409.1 | 236-335 |
| RAB25 | NM_020387.2 | 246-345 | SFRP1 | NM_003012.3 | 3321-3420 |
| RAB35 | NM_001167606.1 | 436-535 | SH2B3 | NM_005475.2 | 4286-4385 |
| RACGAP1 | NM_013277.3 | 10-109 | SHC1 | NM_001130040.1 | 1986-2085 |
| RAD17 | NM_002873.1 | 26-125 | SLC16A3 | NM_001042422.1 | 390-489 |
| RAD50 | NM_005732.2 | 5398-5497 | SLC25A19 | NM_001126121.1 | 1086-1185 |
| RAD51 | NM_001164269.1 | 751-850 | SLC39A6 | NM_001099406.1 | 1041-1140 |
| RAD51L1 | NM_002877.4 | 91-190 | SLC40A1 | NM_014585.5 | 1666-1765 |
| RAD51C | NM_002876.2 | 301-400 | GPR172A | NM_024531.3 | 941-1040 |
| RAF1 | NM_002880.2 | 1991-2090 | SLC5A6 | NM_021095.1 | 1456-1555 |
| RAI2 | NM_021785.3 | 1606-1705 | SLC7A6 | NM_001076785.1 | 2111-2210 |
| RANBP1 | NM_002882.2 | 381-480 | SLC9A3 | NM_004174.2 | 736-835 |
| RARA | NM_000964.2 | 116-215 | SLC9A3R1 | NM_004252.3 | 1811-1910 |
| RB1 | NM_000321.1 | 2111-2210 | C4orf34 | NM_174921.1 | 371-470 |
| SMO | NM_005631.3 | 1616-1715 | TMEM208 | NM_014187.3 | 141-240 |
| SNAI1 | NM_005985.2 | 64-163 | TMEM25 | NM_001144034.1 | 1053-1152 |
| SNRPA1 | NM_003090.2 | 120-219 | TMEM45B | NM_138788.3 | 2076-2175 |
| SNRPD1 | NM_006938.2 | 1205-1304 | TNFRSF11A | NM_003839.2 | 491-590 |
| SPAG5 | NM_006461.3 | 511-610 | TNFSF11 | NM_003701.2 | 491-590 |
| SPATA7 | NM_001040428.2 | 1006-1105 | TOM1L1 | NM_005486.2 | 1431-1530 |
| SPDEF | NM_012391.1 | 1336-1435 | TOMM40 | NM_001128916.1 | 1585-1684 |
| SPINT1 | NM_001032367.1 | 1316-1415 | TOP2A | NM_001067.2 | 5377-5476 |
| SPINT2 | NM_001166103.1 | 626-725 | TOR1A | NM_000113.2 | 626-725 |
| SQLE | NM_003129.3 | 251-350 | TP53 | NM_000546.2 | 1331-1430 |
| SRC | NM_005417.3 | 176-275 | TP53BP2 | NM_001031685.2 | 1541-1640 |
| ST18 | NM_014682.2 | 1296-1395 | TP63 | NM_001114978.1 | 1176-1275 |
| STAT1 | NM_007315.2 | 206-305 | TRIM29 | NM_012101.3 | 2646-2745 |
| STAT3 | NM_003150.3 | 2061-2160 | TRIP13 | NM_001166260.1 | 951-1050 |
| STC2 | NM_003714.2 | 2826-2925 | TSHZ1 | NM_005786.4 | 4466-4565 |
| STK11 | NM_000455.4 | 2061-2160 | TSPAN13 | NM_014399.3 | 556-655 |
| STK38L | NM_015000.1 | 421-520 | TTK | NM_001166691.1 | 776-875 |
| STMN1 | NM_001145454.1 | 811-910 | TUBA4A | NM_006000.1 | 218-317 |
| STRAP | NM_007178.3 | 1536-1635 | TUBB6 | NM_032525.1 | 1396-1495 |
| SUV39H2 | NM_024670.3 | 2036-2135 | TWIST1 | NM_000474.3 | 36-135 |
| TACC3 | NM_006342.1 | 154-253 | TWIST2 | NM_057179.1 | 1266-1365 |
| TAP1 | NM_000593.5 | 2076-2175 | TYMP | NM_001953.3 | 720-819 |
| TCEAL1 | NM_001006639.1 | 471-570 | TYMS | NM_001071.1 | 556-655 |
| TCF7L1 | NM_031283.1 | 2216-2315 | UBE2C | NM_007019.2 | 562-661 |
| TFAM | NM_003201.1 | 86-185 | UBE2T | NM_014176.3 | 596-695 |
| TFF1 | NM_003225.2 | 211-310 | UCHL1 | NM_004181.3 | 451-550 |
| TFF3 | NM_003226.2 | 582-681 | UIMC1 | NM_016290.3 | 996-1095 |
| TFRC | NM_001128148.1 | 2041-2140 | USP10 | NM_005153.2 | 1921-2020 |
| TGFBR2 | NM_001024847.1 | 1761-1860 | VAMP8 | NM_003761.3 | 261-360 |
| TGFBR3 | NM_003243.3 | 1951-2050 | VAV3 | NM_001079874.1 | 353-452 |
| THBS1 | NM_003246.2 | 3466-3565 | VEGFA | NM_001025366.1 | 1326-1425 |
| THY1 | NM_006288.2 | 136-235 | VIM | NM_003380.2 | 695-794 |
| TIMM17A | NM_006335.2 | 86-185 | WDR12 | NM_018256.3 | 656-755 |
| TIMM8A | NM_001145951.1 | 411-510 | WDR4 | NM_018669.4 | 1636-1735 |
| TK1 | NM_003258.1 | 1216-1315 | WIPF2 | NM_133264.4 | 1801-1900 |
| TM7SF3 | NM_016551.2 | 1316-1415 | XBP1 | NM_001079539.1 | 936-1035 |
| TMCC2 | NM_014858.2 | 2793-2892 | YBX1 | NM_004559.3 | 541-640 |
| TMEM125 | NM_144626.1 | 956-1055 | CSDA | NM_001145426.1 | 658-757 |

TABLE 8-continued nCounter ™ CodeSet Design for the 560 genes

| Gene | Accession | T.Region | Gene | Accession | T.Region |
| --- | --- | --- | --- | --- | --- |
| TMEM139 | NM_153345.1 | 1416-1515 | ZEB1 | NM_001128128.1 | 1451-1550 |
| TMEM158 | NM_015444.2 | 1271-1370 | ZEB2 | NM_014795.2 | 21-120 |
| ZNF217 | NM_006526.2 | 1221-1320 | | | |

"T. region": target region;
h. hypothetical protein;
"s. Cytokeratin-8": similar to Keratin type II cytoskeletal 8 (Cytokeratin-8) (CK-8) (Keraton-8) (K8);
"h. MGC18216": hypothetical protein MGC18216.

The invention claimed is:

1. A treatment method comprising:
   (a) quantifying HER2 mRNA in an isolated biological sample of a human patient with HER2+ breast cancer:
      (i) before starting the anti-HER2 therapy in the absence of chemotherapy, and
      (ii) at day 14 after the initiation of the anti-HER2 therapy in the absence of chemotherapy;
   (b) calculating a ratio between the log 2 expression value of the HER2 mRNA quantified in step (ii) and the log 2 expression value of the HER2 mRNA quantified in step (i);
   (c) identifying the patient as having a non-responder phenotype to anti-HER2 therapy, which is a patient where said ratio is equal to or higher than −0.35; and
   (d) administering an alternative medical regimen to the patient having a non-responder phenotype to anti-HER2 therapy;
      wherein the alternative medical regimen is chemotherapy, surgery, radiotherapy, or any combination thereof; and
      wherein the anti-HER2 therapy is trastuzumab and lapatinib.

2. The method according to claim 1 wherein the chemotherapy is selected from the group comprising: paclitaxel, docetaxel, carboplatin, doxorubicin, epirubicin, nab-paclitaxel, vinorelbine, capecitabine and eribulin, or any combination thereof.

3. The method according to claim 1 wherein the sample is an isolated breast tissue sample.

4. The method according to claim 1 wherein the patient is a woman.

5. The method according to claim 1 wherein patient is hormone receptor-positive (HR+) patient and the anti-HER2 therapy is combined with endocrine therapy.

6. The method according to claim 5 wherein the endocrine therapy is selected from the group comprising: tamoxifen, toremifene, anastrozole, exemestane, letrozole, fulvestrant, goserelin, leuprolide, triptorelin, or any combinations thereof.

* * * * *